US012616846B2

(12) United States Patent
Suehara et al.

(10) Patent No.: US 12,616,846 B2
(45) Date of Patent: May 5, 2026

(54) TREATMENT APPARATUS AND TREATMENT METHOD

(71) Applicant: TERUMO KABUSHIKI KAISHA, Tokyo (JP)

(72) Inventors: Satoru Suehara, Kanagawa (JP); Mayu Hata, Yokohama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 363 days.

(21) Appl. No.: 17/943,780

(22) Filed: Sep. 13, 2022

(65) Prior Publication Data

US 2023/0001226 A1    Jan. 5, 2023

Related U.S. Application Data

(63) Continuation of application No. PCT/JP2021/009428, filed on Mar. 10, 2021.

(30) Foreign Application Priority Data

Mar. 30, 2020    (JP) ................................. 2020-060400

(51) Int. Cl.
*A61N 5/06*        (2006.01)
(52) U.S. Cl.
CPC .... *A61N 5/0601* (2013.01); *A61N 2005/0611* (2013.01); *A61N 2005/063* (2013.01)
(58) Field of Classification Search
CPC .......... A61N 5/0601; A61N 2005/0611; A61N 2005/063
See application file for complete search history.

(56) References Cited

U.S. PATENT DOCUMENTS

| | | | |
|---|---|---|---|
| 5,947,958 A | 9/1999 | Woodard et al. | |
| 6,626,900 B1 | 9/2003 | Sinofsky et al. | |
| 7,338,430 B2 * | 3/2008 | Lim ..................... | A61N 5/1016 600/7 |
| 11,033,753 B2 * | 6/2021 | Otsu ................... | A61N 5/0603 |
| 11,583,694 B2 * | 2/2023 | Otsu ................... | A61N 5/0603 |

(Continued)

FOREIGN PATENT DOCUMENTS

| | | |
|---|---|---|
| JP | 2003518395 A | 6/2003 |
| JP | 2009535116 A | 10/2009 |

(Continued)

OTHER PUBLICATIONS

International Search Report (PCT/ISA/210) with translation and Written Opinion (PCT/ISA/237) mailed on Apr. 27, 2021, by the Japan Patent Office as the International Searching Authority for International Application No. PCT/JP2021/009428. (11 pages).

*Primary Examiner* — Baisakhi Roy

(74) *Attorney, Agent, or Firm* — Buchanan Ingersoll & Rooney PC

(57)            ABSTRACT

A treatment apparatus and a treatment method capable of effectively treating cancer including a cervix. The treatment apparatus includes: a main shaft including a distal portion and a proximal portion; an inflation portion disposed on a distal side of the main shaft and configured to be inflated by inflowing a fluid; a distal shaft protruding from the inflation portion toward the distal side; and at least one irradiation unit configured to emit excitation light of an antibody-photosensitive substance from the distal shaft and the inflation portion.

20 Claims, 10 Drawing Sheets

(56) References Cited

U.S. PATENT DOCUMENTS

| 2002/0087205 | A1* | 7/2002 | Chen | A61K 41/0061 |
| | | | | 606/9 |
| 2003/0114434 | A1* | 6/2003 | Chen | A61P 35/02 |
| | | | | 604/20 |
| 2016/0228568 | A1* | 8/2016 | de los Pinos | C12N 7/00 |
| 2017/0050043 | A1 | 2/2017 | Kang et al. | |
| 2018/0113246 | A1* | 4/2018 | Rose | G02B 27/0927 |
| 2018/0369603 | A1* | 12/2018 | Gj?rsvik | A61N 5/0603 |
| 2021/0052914 | A1* | 2/2021 | Yoshino | A61N 5/0603 |
| 2022/0047331 | A1* | 2/2022 | Takata | A61N 5/0601 |
| 2023/0001226 | A1* | 1/2023 | Suehara | A61N 5/062 |
| 2023/0021096 | A1* | 1/2023 | Suehara | A61N 5/062 |

FOREIGN PATENT DOCUMENTS

| JP | 2018538077 | A | 12/2018 |
| WO | 2008066943 | A2 | 6/2008 |
| WO | 2016031875 | A1 | 3/2016 |

* cited by examiner

*FIG.2A*
*FIG.2B*
*FIG.3A*
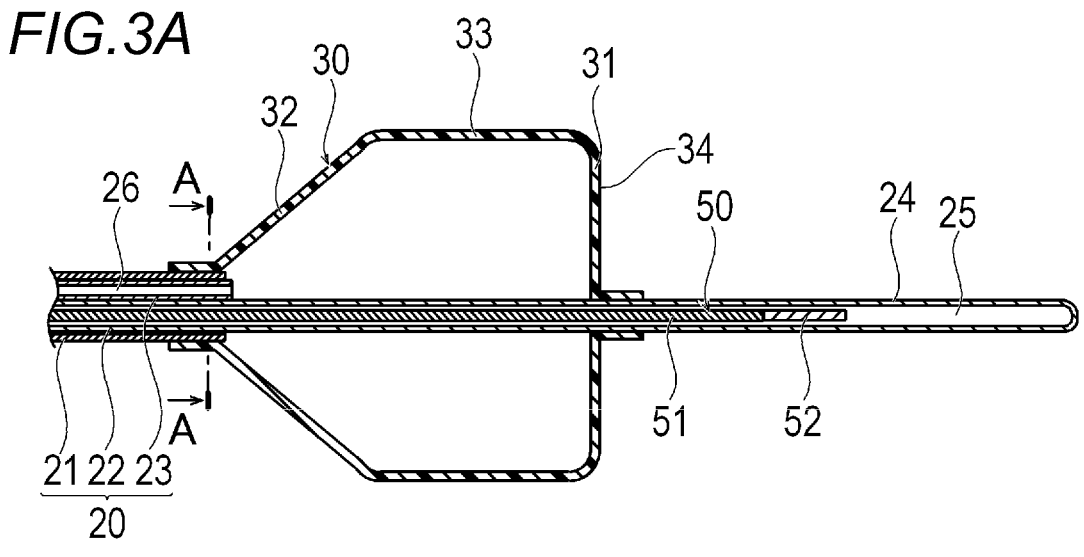
*FIG.3B*
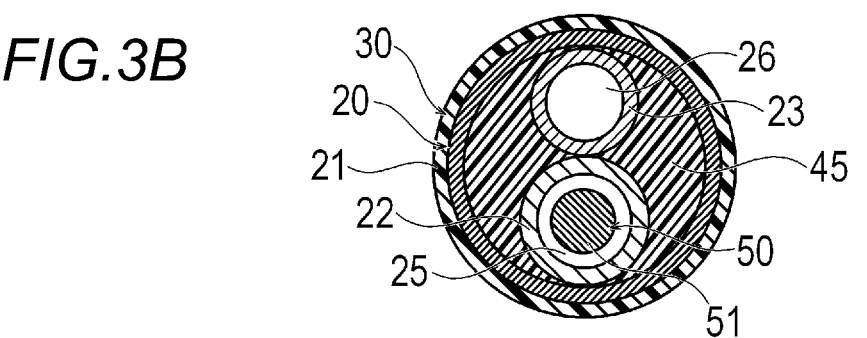

*FIG.6A*
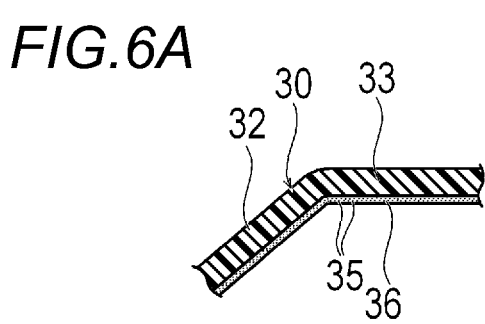
*FIG.6B*
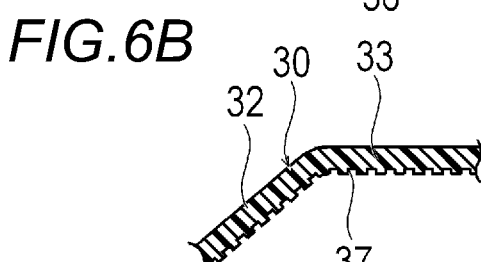
*FIG.6C*
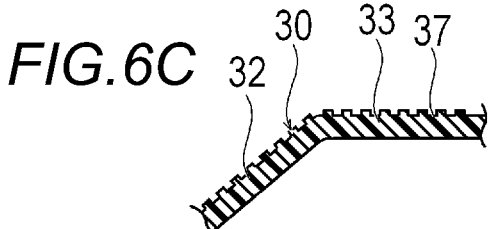
*FIG.6D*
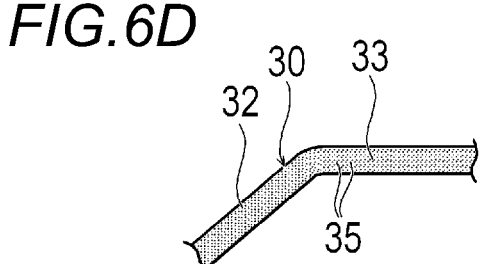
*FIG.6E*
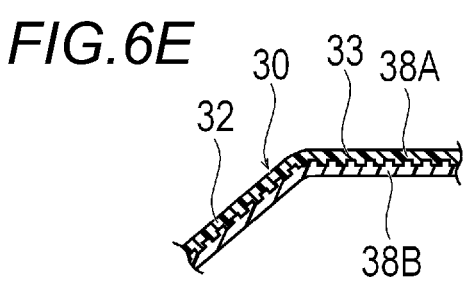
*FIG.7A*
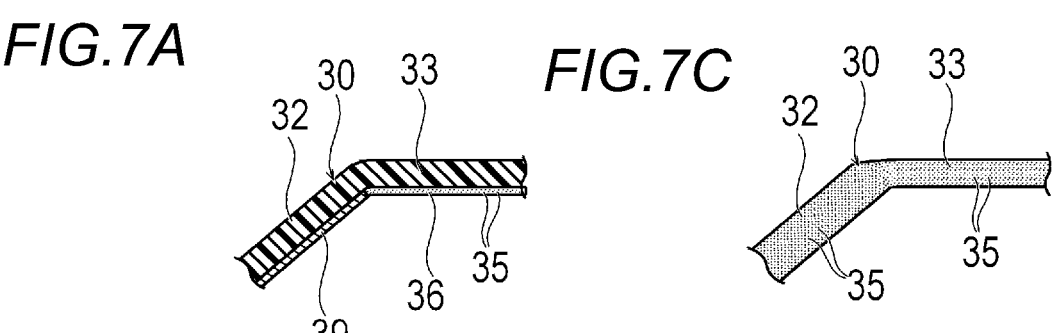
*FIG.7C*
*FIG.7B*
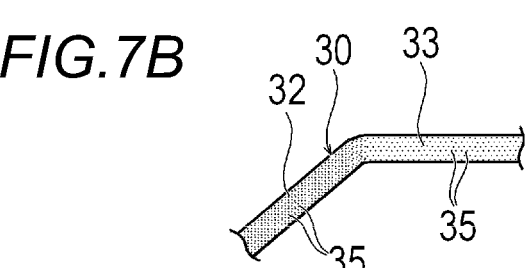

TREATMENT APPARATUS AND TREATMENT METHOD

CROSS-REFERENCES TO RELATED APPLICATIONS

This application is a continuation of International Application No. PCT/JP2021/009428 filed on Mar. 10, 2021, which claims priority to Japanese Application No. 2020-060400 filed on Mar. 30, 2020, the entire content of both of which is incorporated herein by reference.

TECHNOLOGICAL FIELD

The present disclosure generally relates to a treatment apparatus and a treatment method for cervical cancer and vaginal cancer.

BACKGROUND DISCUSSION

The number of patients with cervical cancer has an increasing tendency, and in particular, the number of young female patients in their 20s and 30s is increasing. In current treatments for cervical cancer, treatment can include removing an entire uterus from an early stage (stage I). However, for young patients, local treatment is required to conserve the uterus in order to maintain fertility. Further, in an advanced stage (stage III and subsequent stages), when cancer has spread to surrounding tissues, it is difficult to remove by surgery, and thus treatment can include combining radiation therapy and chemotherapy. However, a five-year survival rate is as low as 50% in stage III and 20% in stage IV, and more effective treatment is required. As the local treatment for cancer, a treatment method using a photoreactive substance is known (for example, see United States Patent Application Publication No. 2018/0113246). In particular, a treatment method using an antibody-photosensitive substance (hydrophilic phthalocyanine) can specifically destroy target cells without destroying non-target cells such as normal cells by irradiating the antibody-photosensitive substance accumulated in a tumor with excitation light (for example, near-infrared rays), and is expected to achieve a relatively high treatment effect while minimizing side effects.

Meanwhile, in order to achieve a high treatment effect by the antibody-photosensitive substance, the antibody-photosensitive substance accumulated in the tumor is required to be reliably irradiated with the near-infrared rays. However, since light is rapidly attenuated due to an influence of a biological tissue, the near-infrared rays have a relatively small penetration depth, and it can be extremely difficult to non-invasively irradiate a solid cancer with light having energy required for treatment from a body surface. Therefore, a method for reliably irradiating the tumor in a body with light while reducing invasiveness as much as possible is required. In the case of cervical cancer, cancer often spreads over a wide area of a cervical canal, and a method for irradiating cancer in a wide range with light from as close as possible is required.

SUMMARY

A treatment apparatus and a treatment method capable of effectively treating cancer in a range including at least a part of a cervix.

A treatment apparatus is disclosed, which is configured to irradiate an antibody-photosensitive substance bound to a tumor cell of cervical cancer with excitation light. The treatment apparatus includes: a main shaft including a distal portion and a proximal portion; an inflation portion disposed on a distal side of the main shaft and configured to be inflated by inflowing a fluid; a distal shaft protruding from the inflation portion toward the distal side; and at least one irradiation unit configured to emit the excitation light of the antibody-photosensitive substance from the distal shaft and the inflation portion.

According to the treatment apparatus described above, the excitation light can be effectively emitted to the antibody-photosensitive substance bound to the tumor cell in a wide range including a cervix in a state in which the distal shaft is inserted into a cervical canal and the inflation portion is inflated in a vagina. Therefore, this treatment apparatus can improve a treatment effect of cancer in a relatively wide range including the cervix.

The distal shaft may emit the excitation light in a direction substantially perpendicular to an axial center of the distal shaft, and the inflation portion may emit the excitation light in a substantially distal direction. Accordingly, the excitation light can be emitted to the tumor cell of the cervix from both the distal shaft and the inflation portion, and thus the treatment effect can be improved.

The treatment apparatus may be formed with an irradiation lumen communicating with an inside of the inflation portion and an inside of the distal shaft and configured to movably accommodate the irradiation unit. Accordingly, even if only one irradiation unit is provided, the excitation light can be emitted from the distal shaft and the inflation portion, and thus a configuration of the treatment apparatus can be simplified and operability can be improved. By moving the irradiation unit, a position where the excitation light is emitted can be appropriately adjusted, and thus the treatment effect can be improved. The number of the irradiation unit is not limited to one.

The inflation portion may have an abutment surface facing the distal side in an inflated state of the inflation portion, and the abutment surface may have a portion that is separated from an axial center of the distal shaft and that partially protrudes toward the distal side. Accordingly, by abutting the inflation portion against the uterine vagina, the portion of the abutment surface that protrudes toward the distal side can be brought close to a vaginal vault. Therefore, the excitation light can be effectively emitted to the vicinity of the vaginal vault, which is difficult for light to reach, and the treatment effect can be improved.

The treatment apparatus may further include an annular reinforcement portion disposed on a distal side of the inflation portion and surrounding a proximal portion of the distal shaft. Accordingly, the distal shaft and the inflation portion can be positioned at appropriate positions by inserting the distal shaft into the cervical canal and abutting the reinforcement portion against the uterine vagina. Therefore, the excitation light can be emitted from the distal shaft and the inflation portion to desired positions, and thus treatment effect can be improved.

The treatment apparatus may further include a detection unit configured to detect fluorescence emitted by the antibody-photosensitive substance. Accordingly, a degree of destruction of the tumor cell due to emission of the excitation light can be checked by a change in the fluorescence detected by the detection unit.

The inflation portion may be configured to move relative to the main shaft in an axial center direction of the main shaft. Accordingly, the distal shaft can be inserted into the cervical canal in a state in which the inflation portion is retracted toward a proximal side with respect to the main shaft to secure a visual field. In a state in which the distal shaft is maintained at an appropriate position of the cervical canal, the inflation portion can be moved and disposed at an appropriate position. Therefore, both the distal shaft and the inflation portion can be accurately and rather easily disposed at appropriate positions of the cervical canal and the vagina. Therefore, the excitation light can be emitted from the distal shaft and the inflation portion to desired positions, and thus the treatment effect can be improved.

A treatment method for, for example, for cervical cancer is disclosed. The treatment method includes: intravenously administering an antibody-photosensitive substance; inserting a treatment apparatus into a living body, for example, a vagina after 12 hours to 36 hours from the intravenous administration, the treatment apparatus including an infla- tion portion configured to be inflated and a distal shaft protruding from the inflation portion and configured to emit excitation light of the antibody-photosensitive substance; inserting the distal shaft into a body lumen, for example, a cervical canal; inflating the inflation portion in the living body or vagina; emitting the excitation light from the distal shaft to a surrounding tissue; emitting the excitation light from the inflation portion to a surrounding tissue; and deflating the inflation portion.

According to the treatment method described above, the distal shaft can be inserted into the cervical canal from an external uterine ostium while visually checking the distal shaft in a state in which the inflation portion is deflated to secure the visual field, and the inflation portion can be widely inflated in the vagina. Therefore, by emitting the excitation light of the antibody-photosensitive substance from the distal shaft and the inflation portion, the excitation light can be effectively emitted to the antibody-photosensi- tive substance bound to the tumor cell in a wide range including the cervix. Therefore, this treatment method can improve the treatment effect of cancer in a wide range including the cervix.

In the emitting of the excitation light from the distal shaft, an irradiation unit configured to emit the excitation light may be disposed inside the distal shaft to emit the excitation light from the irradiation unit, in the emitting of the exci- tation light from the inflation portion, the irradiation unit may be disposed inside the inflation portion to emit the excitation light from the irradiation unit, and the irradiation unit may be moved between the distal shaft and the inflation portion between the emitting of the excitation light from the distal shaft and the emitting of the excitation light from the inflation portion. Accordingly, even if only one irradiation unit is provided, the excitation light can be emitted from the distal shaft and the inflation portion, and thus the configu- ration of the treatment apparatus can be simplified and the operability can be improved. By moving the irradiation unit, a position where the excitation light is emitted can be appropriately adjusted, and thus the treatment effect can be improved. An order of emitting the excitation light is not limited. Therefore, the excitation light may be emitted from the distal shaft first, or the excitation light may be emitted from the inflation portion first. The number of the irradiation unit is not limited to one.

The emitting of the excitation light from the distal shaft and the emitting of the excitation light from the inflation portion may be performed simultaneously. Accordingly, this treatment method can simultaneously emit the excitation light from various positions and directions, and thus the treatment effect can be improved, and treatment can be efficiently performed in a short time.

In the inserting of the distal shaft into the cervical canal, an abutment surface may be abutted against a uterine vagina. The abutment surface may be disposed on a proximal side of the distal shaft. The distal shaft may extend from the abutment surface and face a distal side. Accordingly, the distal shaft and the inflation portion can be positioned at appropriate positions. Therefore, the excitation light can be emitted from the distal shaft and the inflation portion to desired positions, and the treatment effect can be improved.

The treatment method may further include detecting fluo- rescence emitted by the antibody-photosensitive substance and checking an intensity of the fluorescence. Accordingly, in this treatment method, the degree of the destruction of the tumor cell due to the emission of the excitation light can be checked by detecting the fluorescence.

The checking of the intensity of the fluorescence may be performed in parallel with the emitting of the excitation light. Accordingly, in this treatment method, a tumor can be treated while detecting the fluorescence to check the degree of the destruction of the tumor cell due to the emission of the excitation light, and the treatment effect can be improved.

The checking of the intensity of the fluorescence may be performed after the emitting of the excitation light. Accord- ingly, in this treatment method, a result of the destruction of the tumor cell due to the emission of the excitation light can be accurately checked by detecting the fluorescence.

A treatment method is disclosed, which includes: intra- venously administering an antibody-photosensitive sub- stance; inserting a treatment apparatus into a living body after the intravenous administration of the antibody-photo- sensitive substance, the treatment apparatus including an inflation portion configured to be inflated and a distal shaft protruding from the inflation portion and configured to emit excitation light of the antibody-photosensitive substance; inserting the distal shaft into a body lumen; inflating the inflation portion in the living body; and emitting the exci- tation light from the distal shaft and the inflation portion to surrounding tissue.

BRIEF DESCRIPTION OF THE DRAWINGS

FIGS. 2A and 2B are schematic views illustrating a vagina and a uterus, in which FIG. 2A illustrates a state of a patient viewed from front, and FIG. 2B illustrates a state of the patient viewed from a left side.

FIGS. 3A and 3B are diagrams illustrating a distal portion of the treatment apparatus according to the embodiment, in which FIG. 3A is a cross-sectional view, and FIG. 3B is a cross-sectional view taken along a line A-A of FIG. 3A.

FIGS. 4A and 4B are plan views illustrating distal shafts according to modifications, in which FIG. 4A illustrates a first modification, and FIG. 4B illustrates a second modifi- cation.

FIGS. 6A to 6E are cross-sectional views illustrating inflation portions according to modifications, in which FIG. 6A illustrates a fourth modification, FIG. 6B illustrates a fifth modification, FIG. 6C illustrates a sixth modification, FIG. 6D illustrates a seventh modification, and FIG. 6E illustrates an eighth modification.

FIGS. 7A to 7C are cross-sectional views illustrating inflation portions according to modifications, in which FIG. 7A illustrates a ninth modification, FIG. 7B illustrates a 10th modification, and FIG. 7C illustrates an 11th modification.

FIGS. 8A to 8F are plan views illustrating inflation portions according to modifications, in which FIG. 8A illustrates a 12th modification, FIG. 8B illustrates a 13th modification, FIG. 8C illustrates a 14th modification, FIG. 8D illustrates a 15th modification, FIG. 8E illustrates a 16th modification, and FIG. 8F illustrates a 17th modification.

FIGS. 9A to 9C are perspective views illustrating reinforcement portions according to modifications, in which FIG. 9A illustrates the 17th modification, FIG. 9B illustrates an 18th modification, and FIG. 9C illustrates a 19th modification.

FIGS. 10A and 10B are plan views illustrating abutment surfaces according to modifications, in which FIG. 10A illustrates a 20th modification, and FIG. 10B illustrates a 21st modification.

FIGS. 11A to 11C are plan views illustrating irradiation units according to modifications, in which FIG. 11A illustrates the present embodiment, FIG. 11B illustrates a 22nd modification, and FIG. 11C illustrates a 23rd modification.

FIGS. 13A and 13B are diagrams illustrating a distal portion of the treatment apparatus according to the 24th modification, in which FIG. 13A is a cross-sectional view, and FIG. 13B is a cross-sectional view taken along a line A-A of FIG. 13A.

DETAILED DESCRIPTION

Figure 1:
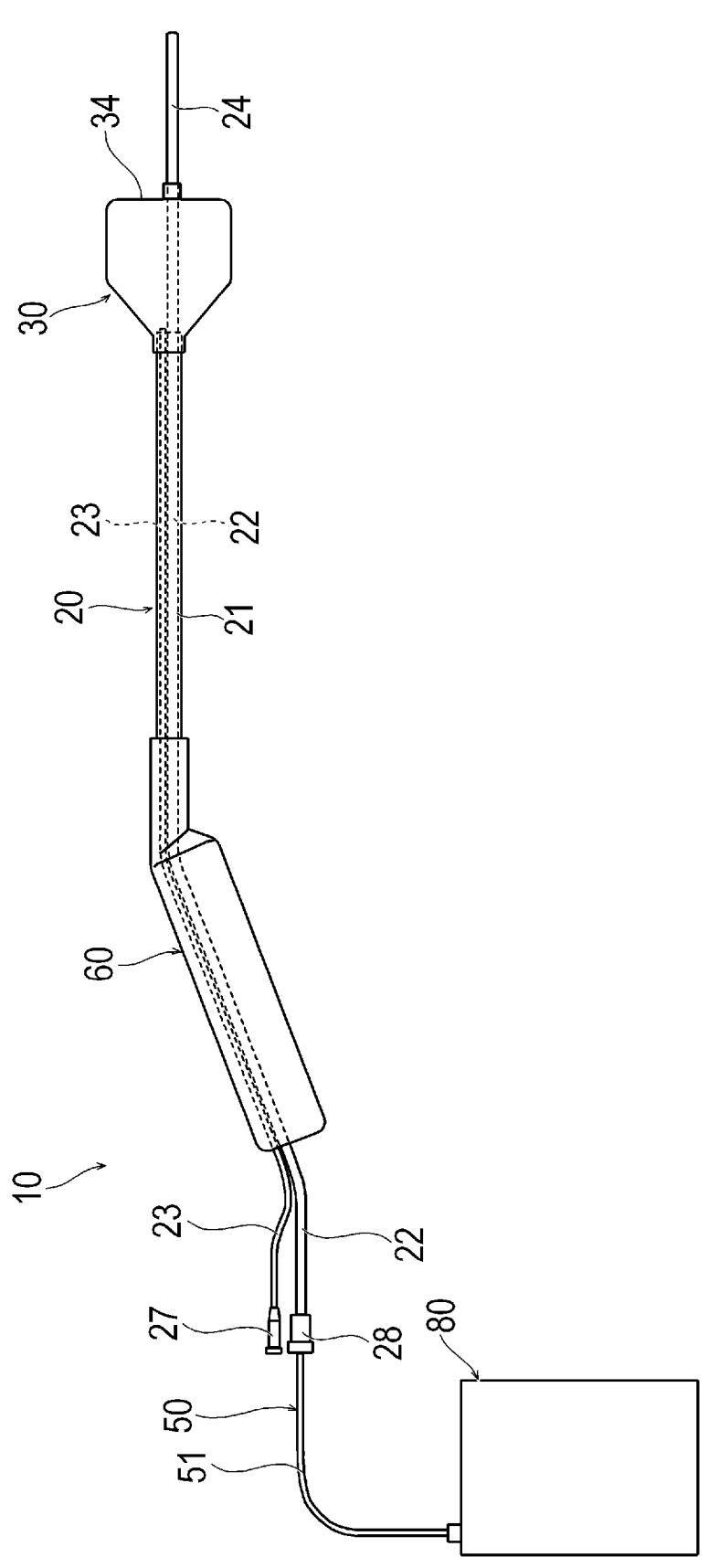
FIG. 1 is a plan view illustrating a treatment apparatus according to an embodiment.

Set forth below with reference to the accompanying drawings is a detailed description of embodiments of a treatment apparatus and a treatment method for cervical cancer and vaginal cancer. Note that since embodiments described below are preferred specific examples of the present disclosure, although various technically preferable limitations are given, the scope of the present disclosure is not limited to the embodiments unless otherwise specified in the following descriptions. For convenience of explanation, dimensions in the drawings may be exaggerated and may be different from actual dimensions. In the present specification and the drawings, components having substantially the same functional configuration are designated by the same reference numerals, and a duplicate description of the components having substantially the same functional configuration will be omitted. In the present specification, a side of a device to be inserted into a body lumen is referred to as a "distal side", and a side to be operated is referred to as a "proximal side".

A treatment apparatus 10 according to the present embodiment is used for a treatment method for cervical cancer. The treatment apparatus 10 and the treatment method can also be used to simultaneously treat both cervical cancer and vaginal cancer. The treatment method can be used for photoimmunotherapy in which an antibody-photosensitive substance bound to cell membranes of target cells is irradiated with near-infrared rays, which serve as excitation light of the antibody-photosensitive substance, to destroy the target cells. The target cells are tumor cells such as cancer cells. In this treatment method, the antibody-photosensitive substance, which is obtained by binding an antibody that specifically binds to only a specific antigen on surfaces of the tumor cells and a photosensitive substance paired with the antibody, is used as a drug. The antibody is not particularly limited, and may be, for example, panitumbab, trastuzumab, HuJ591, pertuzumab, lapatinib, palbociclib, and olaparib. The photosensitive substance can be, for example, hydrophilic phthalocyanine which is a substance that reacts with near-infrared rays having a wavelength of about 700 nm (IR700), but is not limited to hydrophilic phthalocyanine. When IR700 receives near-infrared rays having a wavelength of about 660 nm to 740 nm, a ligand of a functional group that secures water solubility is broken, causing a structural change of the IR700 from water-soluble to hydrophobic. Due to this structural change, membrane protein is extracted, holes are opened in the cell membranes, and water enters the cells, so that the cancer cells can be ruptured and destroyed. IR700 can be excited by receiving the near-infrared rays, and emits fluorescence having a wavelength different from an excitation wavelength. For example, IR700 emits fluorescence having a wavelength of 704 nm when excited by receiving near-infrared rays having a wavelength of 689 nm. A structural change of the IR700 occurs while emitting the fluorescence by a photoreaction, and IR700 also stops emitting the fluorescence when the tumor cells are destroyed and the role as a drug is finished.

The treatment apparatus 10 illustrated in FIG. 1 can treat, with one device, cervical cancer and vaginal cancer in a relatively wide range A, which is illustrated in FIGS. 2A, 2B, 14, 15, and 16 and can include a cervix U, an external uterine ostium O, a uterine vagina UV around the external uterine ostium O, a vaginal vault VF, and a site or location near the vaginal vault VF on a vaginal introitus side relative to the vaginal vault VF of a vagina V. The treatment apparatus 10 can emit the excitation light to the antibody-photosensitive substance bound to tumor cells C in a relatively wide range from the cervix U to the vagina V.

A uterus is positioned behind the vagina V, an upper portion of the uterus is connected to left and right fallopian tubes, and the external uterine ostium O at a lower portion of the uterus is connected to the vagina V. The uterus is roughly divided into a uterine corpus and the cervix U, and the cervix U includes a cervical canal CC connected to the external uterine ostium O. The vagina V includes the vaginal vault VF that extends around the external uterine ostium O. The vaginal vault VF is deeper at a posterior vaginal vault RV positioned in a posterior part of the vagina V than at an anterior vaginal vault AV positioned at an anterior part of the vagina V.

First, the treatment apparatus 10 according to the present embodiment will be described.

As illustrated in FIGS. 1, 3A, and 3B, the treatment apparatus 10 can include an elongated shaft portion 20 including a distal portion and a proximal portion, an inflation portion 30 which is a balloon provided at the distal portion of the shaft portion 20, an operation portion 60 connected to the proximal portion of the shaft portion 20, and an elongated irradiation unit 50 that emits light. The treatment apparatus 10 can be used by being connected to a light output device 80.

The shaft portion 20 includes a main shaft 21 which can be a tubular body extending from the operation portion 60 in a distal direction, an irradiation shaft 22 that accommodates the irradiation unit 50, and a flow path shaft 23 through which a fluid such as a gas or a liquid for inflating the inflation portion 30 flows.

The main shaft 21 can be a tubular body that supports the inflation portion 30. The main shaft 21 accommodates the irradiation shaft 22 and the flow path shaft 23 in a lumen of the main shaft 21. The main shaft 21 can be a circular tube extending linearly, but may be bent or may not be a circular tube. A proximal portion of the main shaft 21 is fixed to the operation portion 60. A distal portion of the main shaft 21 is fixed to a proximal portion of the inflation portion 30. A sealing member 45 that isolates an inside of the main shaft 21 from an inside of the inflation portion 30 is disposed inside the distal portion of the main shaft 21. The sealing member 45 helps prevent the fluid from flowing from the inside of the inflation portion 30 into the lumen of the main shaft 21.

The main shaft 21 preferably has a certain degree of rigidity such that an operator can hold the operation portion 60 and push the main shaft 21 to a desired position in the living body. A constituent material for the main shaft 21 is not particularly limited, and the material for the main shaft 21 can include: a metal represented by stainless steel, aluminum, titanium alloys, tin, magnesium alloys, or the like; a resin represented by polyetheretherketone (PEEK), polyamide, acrylonitrile butadiene styrene (ABS), polycarbonate, polyacetal, polyimide; or the like. A length of the main shaft 21 in an axial center direction is not particularly limited, and can be, for example, 100 mm to 400 mm.

The irradiation shaft 22 is a tubular member capable of accommodating the irradiation unit 50 in the irradiation shaft 22, and capable of transmitting light from the irradiation unit 50 outward. A part of the irradiation shaft 22 is disposed inside the main shaft 21 and the inflation portion 30. A distal portion of the irradiation shaft 22 extends toward the distal side relative to the main shaft 21 and the inflation portion 30. A portion of the irradiation shaft 22 protruding toward the distal side relative to the inflation portion 30 is a distal shaft 24. The distal shaft 24 is a portion to be inserted from the external uterine ostium O into the cervical canal CC in order to emit light from an inside of the cervical canal CC to the cervix U (see FIG. 14). A proximal portion of the irradiation shaft 22 extends toward the proximal side relative to the main shaft 21 and the operation portion 60. An irradiation lumen 25 in which the irradiation unit 50 is movable can be formed inside the irradiation shaft 22. The irradiation lumen 25 is closed at a most distal end of the irradiation shaft 22, and is opened at a most proximal end of the irradiation shaft 22. An insertion port 28 for receiving the irradiation unit 50 into the irradiation lumen 25 is disposed on a proximal side of the irradiation shaft 22.

The irradiation shaft 22 can be formed of a transparent or translucent material capable of transmitting light having a wavelength emitted by the irradiation unit 50 accommodated in the irradiation shaft 22. A constituent material for the irradiation shaft 22 is not particularly limited, and can include: a resin represented by polymethyl methacrylate, polyethylene terephthalate, polycarbonate, polytetrafluoroethylene, or the like; glass; or the like. It can be more preferable that a material for the distal shaft 24 has elasticity and has a physical property allowing the distal shaft 24 to be deformed while being bent along a cervical canal after being inserted into the cervical canal. Accordingly, it is possible to cope with individual differences in a shape of the cervical canal, and it is possible to reduce a burden on an inner surface of the cervical canal and to further improve adhesion to the inner surface of the cervical canal. An outer diameter of the irradiation shaft 22 (the distal shaft 24) is not particularly limited, and can be, for example, 0.5 mm to 6 mm. A length of the distal shaft 24 in the axial center direction is not particularly limited, and can be, for example, 10 mm to 50 mm. The distal shaft 24 may have a function of diffusing light. Therefore, similarly to the inflation portion 30 described in detail later, the distal shaft 24 may contain scatterers in at least a part of the constituent material, may have multiple irregularities formed on an inner surface or an outer surface of distal shaft 24, or may have a multi-layer structure in which materials having different refractive indexes are joined by a surface on which multiple irregularities are formed. The distal shaft 24 can be formed to be rigid, substantially rigid, or flexible.

Figure 4A:
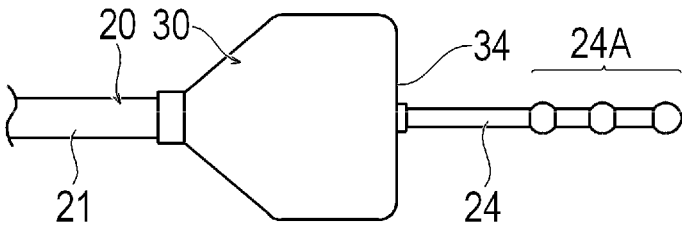

A shape of the distal shaft 24 is not particularly limited. For example, as in a first modification illustrated in FIG. 4A, the distal shaft 24 may include irregular structures 24A arranged in the axial center direction. Accordingly, when inserting the distal shaft 24 from the external uterine ostium O into the cervical canal CC, the operator can rather easily grasp a length of insertion of the distal shaft 24 into the cervical canal CC by visually checking the irregular structure 24A. When inserting the irregular structure 24A from the external uterine ostium O into the cervical canal CC, the operator can rather easily grasp the length of insertion of the distal shaft 24 into the cervical canal CC based on a change in sensation received by a hand holding the operation portion 60. As a structure that facilitates visual check, the distal shaft 24 may have a line, a notch, or the like serving as a scale. The distal shaft 24 may have physical properties that change along the axial center direction such that the sensation received by the hand of the operator changes when the operator inserts the distal shaft 24 from the external uterine ostium O into the cervical canal CC. For example, the distal shaft 24 may have a decrease in rigidity toward the distal direction, or may have high-rigidity portions and low-rigidity portions that are alternately arranged.

Figure 4B:
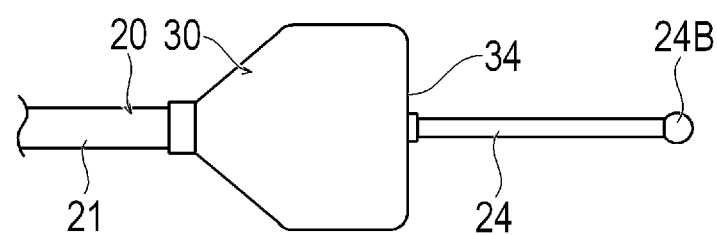

As in a second modification illustrated in FIG. 4B, the distal shaft 24 may include a distal portion provided with one large-diameter portion 24B having a relatively large outer diameter. Accordingly, after inserting the distal shaft 24 from the external uterine ostium O into the cervical canal CC, the operator can rather easily grasp, based on the change in the sensation received by the hand holding the operation portion 60, that the large-diameter portion 24B crosses an internal cervical ostium I and reaches a uterine cavity UC. For example, the operator can retract the operation portion 60 and bring the large-diameter portion 24B into contact with the internal cervical ostium I after the large-diameter portion 24B crossed the internal cervical ostium I. Therefore, the distal shaft 24 including the large-diameter portion 24B can be effective when it is desired to accurately position the distal portion of the distal shaft 24 with respect to the internal cervical ostium I, or when it is desired to reliably pass the distal portion of the distal shaft 24 through the internal cervical ostium I. A position of the large-diameter portion 24B is not limited to a most distal end of the distal shaft 24.

Figure 5:
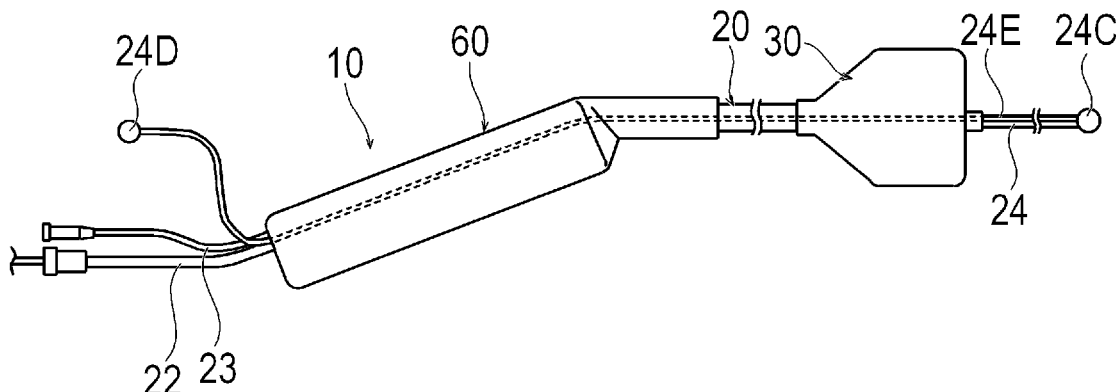
FIG. 5 is a plan view illustrating a third modification.

As in a third modification illustrated in FIG. 5, the distal shaft 24 may include a distal portion provided with a bag-shaped first balloon 24C that is flexibly deformable. The first balloon 24C communicates with a bag-shaped second balloon 24D disposed on the operation portion 60 by a tube 24E. A fluid such as a gas or a liquid is sealed in the first balloon 24C, the second balloon 24D, and the tube 24E. Accordingly, when the distal shaft 24 enters the cervical canal CC from the external uterine ostium O, the first balloon 24C is compressed, the fluid inside the first balloon 24C moves toward the second balloon 24D, and the second balloon 24D is inflated. Accordingly, the operator can rather easily grasp, by viewing the second balloon 24D, that the distal shaft 24 including the first balloon 24C enters the cervical canal CC. When the first balloon 24C crosses the internal cervical ostium I, the first balloon 24C is inflated due to a restoring force per se, the fluid inside the second balloon 24D moves toward the first balloon 24C, and the second balloon 24D becomes smaller. Accordingly, the operator can rather easily grasp, by viewing the second balloon 24D, that the distal shaft 24 including the first balloon 24C crosses the internal cervical ostium I.

The operator may insert the distal shaft 24 from the external uterine ostium O into the cervical canal CC in a state in which the irradiation unit 50 disposed inside the distal shaft 24 is caused to emit light. Light emitted from a portion of the distal shaft 24 inserted into the cervical canal CC is invisible to the operator. Therefore, the operator can rather easily visually grasp the length of insertion of the distal shaft 24 into the cervical canal CC. In this case, even if the distal shaft 24 is not provided with the irregular structure 24A or the large-diameter portion 24B, the operator can visually grasp the length of insertion of the distal shaft 24 into the cervical canal CC.

As illustrated in FIGS. 1, 3A, and 3B, the flow path shaft 23 is disposed inside the main shaft 21. A distal portion of the flow path shaft 23 is positioned near the distal portion of the main shaft 21. A proximal portion of the flow path shaft 23 extends toward the proximal side relative to the main shaft 21 and the operation portion 60. An inflation lumen 26, through which an inflation fluid for inflating the inflation portion 30 flows, is formed inside the flow path shaft 23. The inflation lumen 26 communicates with the inside of the inflation portion 30. The proximal portion of the flow path shaft 23A is provided with a port 27 to which a syringe or an indeflator (i.e., inflation/deflation device) for supplying the inflation fluid is connectable.

The inflation portion 30 is a member that is disposed on a proximal side of the distal shaft 24 to be inserted into the cervical canal CC, and is capable of being inflated in the vagina V and emitting light in a wide range of the vagina V. The inflation portion 30 can transmit outward light emitted from the irradiation unit 50 disposed in the irradiation lumen 25 passing through the inside of the inflation portion 30. Therefore, the inflation portion 30 can be formed of a transparent or translucent material capable of transmitting light having a wavelength emitted by the irradiation unit 50.

A distal side of the inflation portion 30 is connected to the irradiation shaft 22, and a proximal side of the inflation portion 30 is connected to the main shaft 21. The inside of the inflation portion 30 communicates with the inflation lumen 26. The inflation portion 30 can be inflatable by being deformed by a fluid inflowing into the inflation portion 30.

The inflation portion 30 can include a distal inflation portion 31 on the distal side, a proximal inflation portion 32 on the proximal side, and an intermediate inflation portion 33 disposed between the proximal inflation portion 32 and the distal inflation portion 31. The distal inflation portion 31 can be fixed to an outer peripheral surface of the irradiation shaft 22. In an inflated state of the inflation portion 30, the distal inflation portion 31 forms a relatively flat abutment surface 34 facing the distal side of the inflation portion 30. The abutment surface 34 is a surface that is substantially perpendicular to an axial center of the shaft portion 20, and abuts against the uterine vagina UV around the external uterine ostium O. A shape of the abutment surface 34 may be changed depending on an internal pressure of the inflation portion 30. For example, when the internal pressure of the inflation portion 30 is relatively high, the abutment surface 34 may have a shape protruding toward the distal side at a position away from the irradiation shaft 22 in a radial direction relative to a position close to the irradiation shaft 22 in the radial direction. The intermediate inflation portion 33 can have a cylindrical shape having a substantially constant outer diameter in the axial center direction between the proximal inflation portion 32 and the distal inflation portion 31. The intermediate inflation portion 33 may not be formed with a substantially constant outer diameter.

A proximal portion of the proximal inflation portion 32 is fixed to an outer peripheral surface of the main shaft 21. In the inflated state, an outer diameter of the proximal inflation portion 32 increases in a tapered shape toward the distal side of the proximal inflation portion 32. A distal portion of the proximal inflation portion 32 is connected to a proximal portion of the intermediate inflation portion 33. The tapered proximal inflation portion 32 prevents the inflation portion 30 from being pushed toward the proximal side and deformed when the distal inflation portion 31 abuts against the uterine vagina UV and receives a reaction force in a proximal direction. The proximal inflation portion 32 may not be formed in a tapered shape.

A constituent material for the inflation portion 30 is not particularly limited as long as the constituent material for the inflation portion 30 has a certain degree of flexibility and can transmit light having a wavelength emitted from the irradiation unit 50, and can be, for example, silicone, polyamide, polyethylene terephthalate, and urethane. A maximum outer diameter of the inflation portion 30 when being inflated is not particularly limited, and can be, for example, 5 mm to 40 mm. A length of the inflation portion 30 in the axial center direction (length direction) when being inflated is not particularly limited, and can be, for example, 10 mm to 60 mm.

The inflation portion 30 may have a structure that scatters the light received from the irradiation unit 50 inside the inflation portion 30. Accordingly, the inflation portion 30 can emit light by the light received from the irradiation unit 50. Therefore, the light can be emitted to a relatively wide range through the inflation portion 30 even in a range other than a range directly irradiated with the light from the irradiation unit 50.

The inflation portion 30 may have a structure that scatters light on an inner surface side of the inflation portion 30. For example, the inflation portion 30 can include, on an inner surface of the inflation portion 30, a scatterer coat 36 including scatterers 35, as in a fourth modification illustrated in FIG. 6A. The scatterer 35 may be implemented by known materials, and may be, for example, fine particles of titanium oxide, styrene, silicone, or the like. The scatterer coat 36 can be coated by mixing the scatterer 35 with a coat substrate having a refractive index different from that of the scatterer 35. As a structure for scattering light, the inflation portion 30 may include, on the inner surface of the inflation portion 30, multiple minute irregular portions 37, as in a fifth modification illustrated in FIG. 6B. As a structure for scattering light, the inflation portion 30 may include, on an outer surface of the inflation portion 30, multiple minute irregular portions 37, as in a sixth modification illustrated in FIG. 6C. When the irregular portions 37 on the outer surface of the inflation portion 30 come into contact with a living body (an organ) such as the uterine vagina UV or the vagina V, the light emitted from the inside of the inflation portion 30 can be relatively easily transmitted to an inside of the living body by the irregular portions 37 without being reflected, and an amount of light inside the inflation portion 30 can be decreased. Therefore, by providing a detection unit 90 (see FIG. 17) capable of detecting the amount of light inside the inflation portion 30, it is possible to determine that the inflation portion 30 is in relatively close contact with the living body. In order to facilitate the transmission of the light to the living body when the irregular portions 37 of the inflation portion 30 come into contact with the living body, a refractive index of the inflation portion 30 is preferably higher than a refractive index of air, and equal to or lower than a refractive index of the living body, and can be, for example, about 1.0 to 1.5.

The inflation portion 30 may have a structure that scatters light inside the material for the inflation portion 30. For example, the inflation portion 30 may include the scatterer 35 inside the material for the inflation portion 30, as in a seventh modification illustrated in FIG. 6D. As in an eighth modification illustrated in FIG. 6E, the inflation portion 30 may have a structure in which a first layer 38A and a second layer 38B having different refractive indexes, which are joined by a surface having irregularities.

The scatterer 35 may be mixed with the inflation fluid supplied to the inside of the inflation portion 30. In this case, the inflation portion 30 may or may not have a structure that scatters light.

The inflation portion 30 may have a structure that increases an irradiation intensity in a specific direction. For example, it may be preferable that the inflation portion 30 does not emit light in the proximal direction and emits light in the radial direction and the distal direction. Accordingly, it is possible to increase an intensity of light that can be emitted from the inflation portion 30 to the tumor cells C of the cervix U or the vagina V close to the cervix U. The structure for increasing the irradiation intensity in the specific direction can be, for example, a structure in which light is less likely to leak outward from the proximal side of the inflation portion 30. For example, the inflation portion 30 may include, on an inner surface of the proximal inflation portion 32, a reflector coat 39 formed of a reflector that reflects light, as in a ninth modification illustrated in FIG. 7A. The reflector may be disposed inside the material for the inflation portion 30 or on the outer surface of the inflation portion 30. In addition, as in a 10th modification illustrated in FIG. 7B, the scatterer 35 may be contained inside the material for the inflation portion 30, and a concentration of the scatterer 35 in the proximal inflation portion 32 may be set to be higher than concentrations of the scatterer 35 in the distal inflation portion 31 and the intermediate inflation portion 33. As in an 11th modification illustrated in FIG. 7C, the scatterer 35 may be contained in the material for the inflation portion 30, and a thickness of the proximal inflation portion 32 may be thicker than thicknesses of the distal inflation portion 31 and the intermediate inflation portion 33.

The inflation portion 30 may be formed in various shapes. For example, it can be preferable that the inflation portion 30 is appropriately selectable according to a shape of the uterine vagina UV, the vaginal vault VF, or the vagina V of the patient.

Figure 8A:
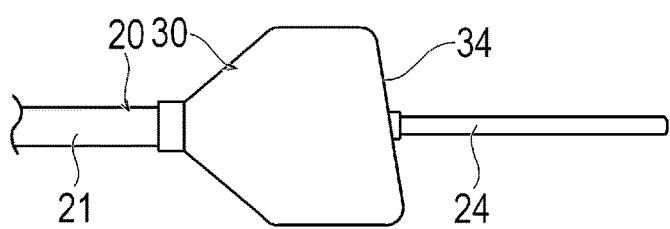

As in a 12th modification illustrated in FIG. 8A, in the inflated state, the abutment surface 34 may be inclined at an angle of less than 90° with respect to a surface perpendicular to the axial center of the shaft portion 20. Accordingly, for example, a portion of the abutment surface 34 that protrudes toward the distal side can be rather easily disposed on a posterior vaginal vault RV side, and a portion on an opposite side of the protruding portion can be rather easily disposed on an anterior vaginal vault AV side. Accordingly, light can be effectively emitted to a range where light is difficult to reach, including the posterior vaginal vault RV and the anterior vaginal vault AV.

Figure 8B:
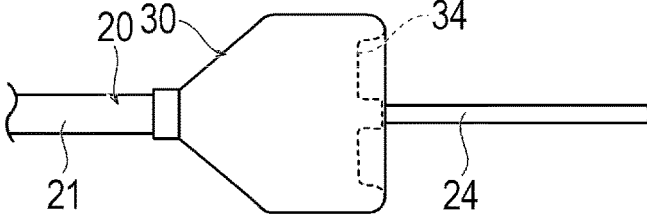

As in a 13th modification illustrated in FIG. 8B, in the inflated state, a central portion (a portion close to the distal shaft 24) of the abutment surface 34 may be formed to be recessed toward the proximal side. Accordingly, the external uterine ostium O is received in the recessed portion of the abutment surface 34, and thus a portion away from the distal shaft 24 in the radial direction (a portion on an outer side in a circumferential direction) of the abutment surface 34 can be effectively brought close to the vaginal vault VF. Therefore, light can be effectively emitted to the vaginal vault VF where light is difficult to reach.

Figure 8C:
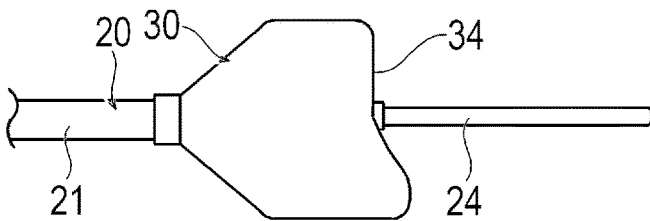

As in a 14th modification illustrated in FIG. 8C, in the inflated state, the abutment surface 34 may have a portion that is separated from the central portion (the portion close to the distal shaft 24) in the radial direction and that partially protrudes toward the distal side, and may have another portion perpendicular to the axial center of the shaft portion 20. As a result, the protruding portion of the abutment surface 34 can be effectively brought close to the vaginal vault VF. Therefore, light can be effectively emitted to the vaginal vault VF where light is difficult to reach.

Figure 8D:
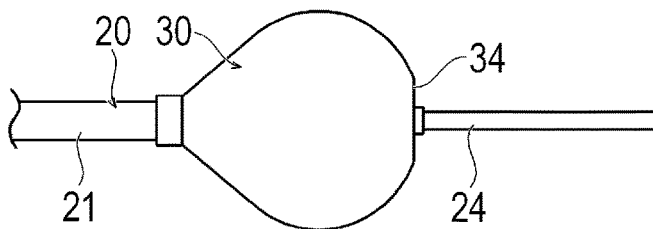

As in a 15th modification illustrated in FIG. 8D, in the inflated state, the central portion (the portion close to the distal shaft 24) of the abutment surface 34 may be perpendicular to the axial center of the shaft portion 20, and a periphery of the perpendicular portion may smoothly protrude outward in the radial direction to form an arc in a cross-section passing through the axial center of the shaft portion 20.

Figure 8E:
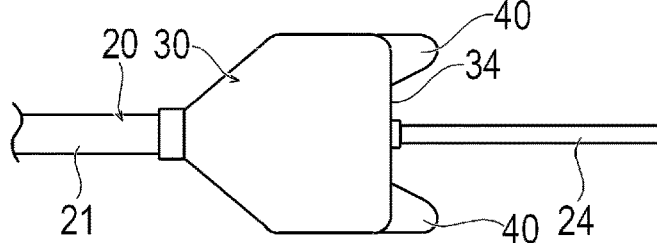

As in a 16th modification illustrated in FIG. 8E, in the inflated state, the central portion (the portion close to the distal shaft 24) of the abutment surface 34 may be perpendicular to the axial center of the shaft portion 20, and a protruding portion 40 protruding toward the distal side may be formed on each of both sides sandwiching the perpendicular portion. The two protruding portions 40 can be formed of a material that is relatively harder than the material for the inflation portion 30 and that transmits light. The two protruding portions 40 can approach two sites (or locations) of the vaginal vault VF sandwiching the external uterine ostium O (for example, the posterior vaginal vault RV and the anterior vaginal vault AV), and can effectively propagate light to the vaginal vault VF where light is difficult to reach. A hardness (a softness) of the material can be specified by, for example, Rockwell hardness, Brinell hardness, Vickers hardness, Shore hardness, and durometer hardness.

Figure 8F:
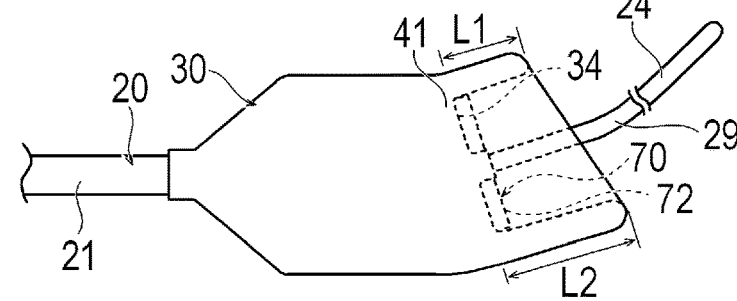

As in a 17th modification illustrated in FIG. 8F, in the inflated state, the inflation portion 30 may include a first bent portion 41 such that an axial center of a distal portion is bent at an angle of less than 90° with respect to an axial center of the proximal portion. In the inflated state, the central portion (the portion close to the distal shaft 24) of the abutment surface 34 is formed to be recessed toward the proximal side. The distal shaft 24 may include a second bent portion 29 such that an axial center of the distal portion is bent at an angle of less than 90° with respect to an axial center of the proximal portion. Accordingly, a distal end of the distal shaft 24 can be displaced from the axial center of the shaft portion 20, and when inserting the distal end of the distal shaft 24 into a uterine ostium under visual confirmation, a better visual field can be ensured. Further, a bending portion of the distal shaft 24 may be substantially consistent with a bending side of the inflation portion 30. This facilitates, for example, inserting the distal shaft 24 into the cervical canal CC which extends in a manner of being inclined with respect to an extending direction of the vagina V. A height L1 from the recessed portion of the abutment surface 34 on a bending direction side of the inflation portion 30 is shorter than a height L2 from the recessed portion of the abutment surface 34 on an opposite side of the bending direction side. Therefore, by disposing the abutment surface 34 on the bending direction side on the anterior vaginal vault AV side and disposing the abutment surface 34 on the opposite side of the bending direction side on the posterior vaginal vault RV side, the abutment surface 34 can be brought close to the entire vaginal vault VF including the anterior vaginal vault AV and the posterior vaginal vault RV. Therefore, light can be effectively emitted to the range where light is difficult to reach, including the posterior vaginal vault RV and the anterior vaginal vault AV. The height L1 from the recessed portion of the abutment surface 34 on the bending direction side of the inflation portion 30 can be, for example, 5 mm to 20 mm. The height L2 from the recessed portion of the abutment surface 34 on the opposite side of the bending direction side of the inflation portion 30 can be, for example, 10 mm to 30 mm. The recessed portion of the abutment surface 34 may or may not be provided with a reinforcement portion 70, which will be described in detail later.

Figure 9A:
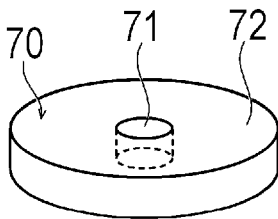

As in the 17th modification illustrated in FIGS. 8F and 9A, the treatment apparatus 10 may include the annular reinforcement portion 70 in a manner of surrounding a proximal portion of the distal shaft 24. The proximal portion of the distal shaft 24 may be a portion of the distal shaft 24 where the distal portion of the inflation portion 30 is joined. The reinforcement portion 70 has an annular shape with a through hole 71, and is formed with constant inner diameter and outer diameter. A constituent material for the reinforcement portion 70 is not particularly limited as long as the constituent material is harder than the inflation portion 30 and can transmit light having a wavelength emitted from the irradiation unit 50, and can be, for example, a resin represented by polymethyl methacrylate, polyethylene terephthalate, polycarbonate, or polytetrafluoroethylene, or glass. Further, a scatterer or a structure that scatters light is preferably provided.

The reinforcement portion 70 is disposed to be in contact with or adjacent to the abutment surface 34 of the inflation portion 30. A second abutment surface 72 (an abutment surface) is formed on a distal side of the reinforcement portion 70. The second abutment surface 72 can abut against the uterine vagina UV together with the abutment surface 34 of the inflation portion 30. When the treatment apparatus 10 is provided with the reinforcement portion 70, the abutment surface 34 of the inflation portion 30 may be abutted against the reinforcement portion 70, and not abutted against the uterine vagina UV. The reinforcement portion 70 can be harder than the inflation portion 30, and thus is less likely to be deformed. Therefore, the inflation portion 30 and the distal shaft 24 can be accurately positioned with respect to the cervix U and the vagina V by abutting the reinforcement portion 70 against the uterine vagina UV. The reinforcement portion 70 may be fixed to the distal shaft 24, or may be slidable along the distal shaft 24.

Figure 9B:
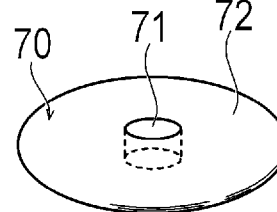
Figure 9C:
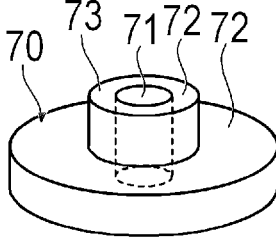

As in an 18th modification illustrated in FIG. 9B, the annular reinforcement portion 70 may have an outer peripheral surface that forms a smooth convex portion on an outer side in the radial direction. As in a 19th modification illustrated in FIG. 9C, the annular reinforcement portion 70 may include a tubular convex portion 73 protruding toward the distal side around the through hole 71. Accordingly, the second abutment surface 72 can be formed with a step. When the abutment surface 34 is abutted against the uterine vagina UV, at least a part of the tubular convex portion 73 rather easily enters the external uterine ostium O. Therefore, the inflation portion 30 and the distal shaft 24 can be accurately positioned with respect to the cervix U and the vagina V by abutting the reinforcement portion 70 including the tubular convex portion 73 against the uterine vagina UV including the external uterine ostium O.

Figure 10A:
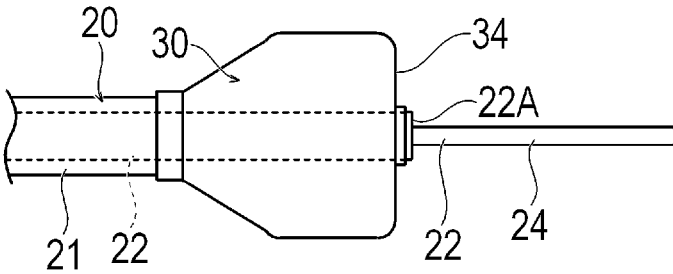

As in a 20th modification illustrated in FIG. 10A, the irradiation shaft 22 may include a step portion in which the outer diameter is increased stepwise at the proximal portion of the distal shaft 24, and a third abutment surface 22A (an abutment surface) facing the distal side of the distal shaft 24 may be formed in the step portion.

Figure 10B:
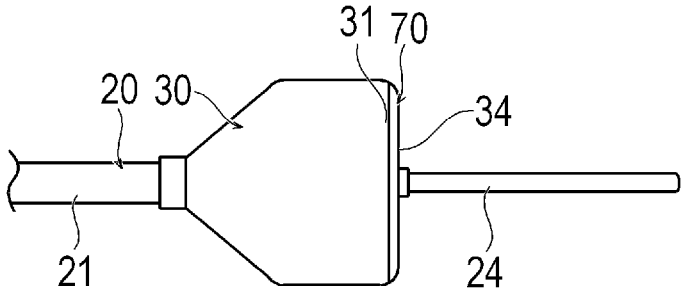

As in a 21st modification illustrated in FIG. 10B, the reinforcement portion 70 may be a member that is fixed to a surface on a distal side of the distal inflation portion 31 to be deformable together with the inflation portion 30 and that transmits light.

As illustrated in FIGS. 1, 3A, and 3B, the irradiation unit 50 can be elongated, and includes at least one optical fiber 51 that propagates light. The irradiation unit 50 includes, at a distal portion of the irradiation unit 50, a light-emitting unit 52 that emits light outward. A proximal portion of the irradiation unit 50 is connectable to the light output device 80 which outputs light. The irradiation unit 50 can receive near-infrared rays from the light output device 80, propagate the near-infrared rays to the light-emitting unit 52, and emit the near-infrared rays from the light-emitting unit 52. The irradiation unit 50 may be formed by an optical waveguide other than the optical fiber.

Figure 11A:
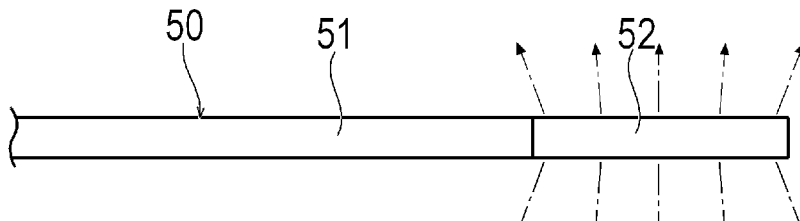
Figure 11B:
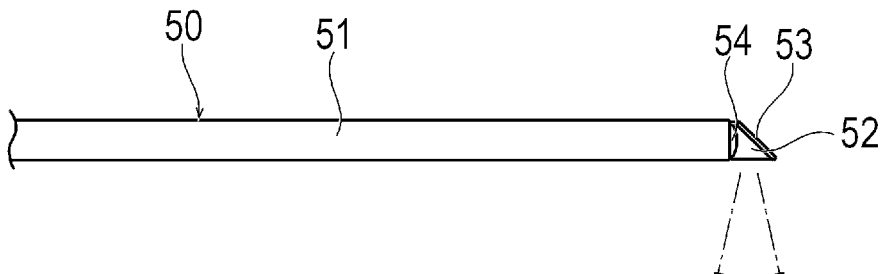

As illustrated in FIG. 11A, the light-emitting unit 52 can be a cylindrical diffuser that is connected to a cut end of the optical fiber 51 and diffuses or scatters light received from the optical fiber 51. The light-emitting unit 52 may be formed integrally with the optical fiber 51 by processing a surface or an inside of the optical fiber 51, or may be the cut end of the optical fiber 51. In this case, it is preferable to provide a plurality of optical fibers 51 to emit light with a wide irradiation angle. The light-emitting unit 52 may be formed by a mirror 53 and/or a lens 54 disposed at the cut end of the optical fiber 51, as in a 22nd modification illustrated in FIG. 11B. By forming the light-emitting unit 52 by the mirror 53 and/or the lens 54, the irradiation angle of light can be widened. By rotating the optical fiber 51, the light-emitting unit 52 can emit light in a wider range.

Figure 11C:
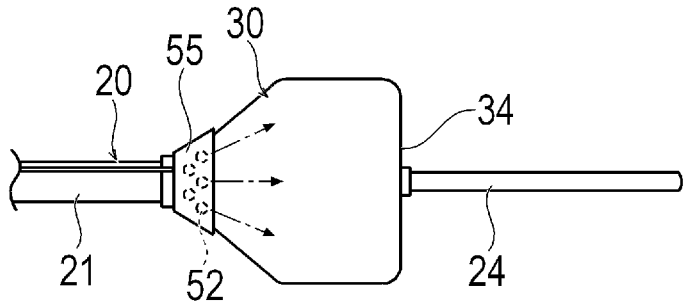

As a method for propagating light to the inflation portion 30, the light-emitting unit 52 may not be disposed inside the shaft portion 20 or may not be disposed inside the inflation portion 30. For example, as in a 23rd modification illustrated in FIG. 11C, the irradiation unit 50 may include an irradiation auxiliary unit 55 that surrounds the shaft portion 20 on the proximal side of the inflation portion 30, and the light-emitting unit 52 may be disposed in the irradiation auxiliary unit 55. The irradiation auxiliary unit 55 has an inner peripheral surface that expands toward the distal direction in a manner of covering a part of the surface of the proximal inflation portion 32 on the proximal side when being inflated. The light-emitting unit 52 is disposed on the inner peripheral surface. The light-emitting unit 52 can be, for example, the end of the optical fiber, the diffuser, the mirror, the lens, and a light-emitting diode (LED) that emits light by electric power. When the light-emitting unit 52 of the irradiation auxiliary unit 55 emits light, light is emitted from the proximal side of the inflation portion 30 to the inside of the inflation portion 30. Accordingly, the inflation portion 30 can emit light substantially as a whole by receiving light from the light-emitting unit 52 of the irradiation auxiliary unit 55. The light-emitting unit 52 provided in the irradiation auxiliary unit 55 may be used together with the irradiation unit 50 provided in the irradiation lumen 25.

The operation portion 60 is a portion to be held and operated by the operator, as illustrated in FIG. 1. The proximal portion of the main shaft 21 is fixed to the operation portion 60. The irradiation shaft 22 and the flow path shaft 23 are led out from a proximal portion of the operation portion 60. The irradiation shaft 22 and the flow path shaft 23 may be fixed at the proximal portion of the operation portion 60. The operation portion 60 is formed to be bent from a distal portion toward the proximal portion to relatively easily secure the visual field of the operator in the vagina V when inserting the inflation portion 30 and the distal shaft 24 from a vaginal introitus. A configuration of the operation portion 60 is not particularly limited.

The light output device 80 can output light having any wavelength to the optical fiber 51 of the irradiation unit 50 with any intensity (power) or energy. The light output device 80 outputs near-infrared rays having a wavelength of, for example, 660 nm to 740 nm, to the optical fiber 51 such that light can be emitted at an intensity (power) of, for example, 1 mW to 5 W, and an energy of, for example, 1 Jcm$^{-2}$ to 50 Jcm$^{-2}$.

Figure 12:
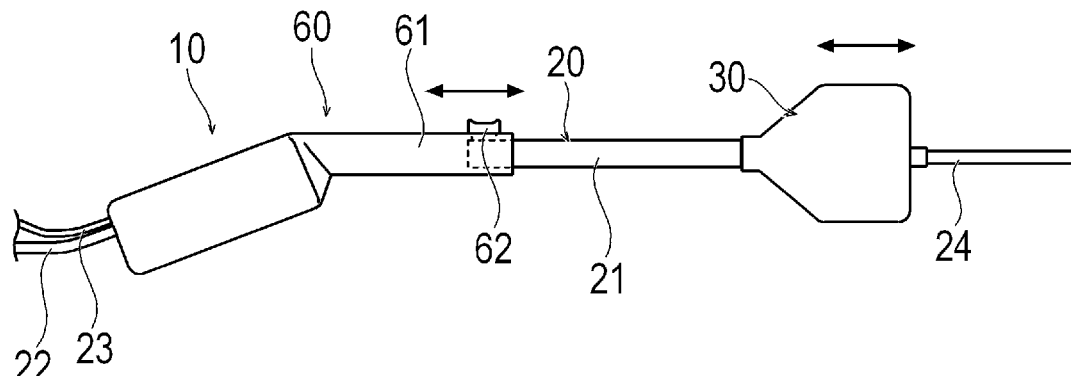
FIG. 12 is a plan view illustrating a treatment apparatus according to a 24th modification.
Figure 13A:
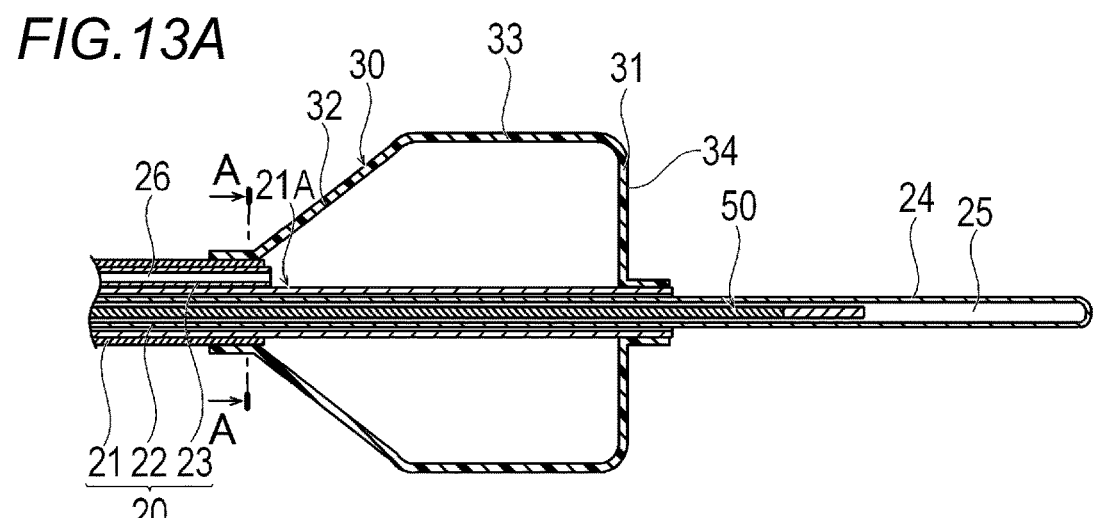
Figure 13B:
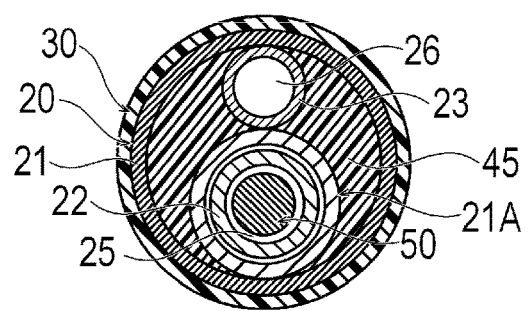

As in a 24th modification illustrated in FIGS. 12, 13A, and 13B, the inflation portion 30 may be movable in the axial center direction with respect to the distal shaft 24. The distal portion of the inflation portion 30 is fixed not to the distal shaft 24 but to a tubular inner shaft 21A that slidably accommodates the distal shaft 24. The inner shaft 21A is fixed to the main shaft 21 by the sealing member 45. The proximal portion of the main shaft 21 is slidable in a casing 61 of the operation portion 60 and is fixed to a movement operation portion 62. The movement operation portion 62 is slidably held with respect to the casing 61. The irradiation shaft 22 including the distal shaft 24 is fixed to the casing 61. When the movement operation portion 62 moves with respect to the casing 61, the irradiation shaft 22 does not move, and the main shaft 21, the flow path shaft 23, the inner shaft 21A, and the inflation portion 30 move with respect to the casing 61. When the treatment apparatus 10 is provided with the reinforcement portion 70, the reinforcement portion 70 also moves together with the inflation portion 30 as the movement operation portion 62 moves. Therefore, after disposing the distal shaft 24 at a desirable position with respect to the cervical canal CC, the operator can move the inflation portion 30 to a desired position by operating the movement operation portion 62 without moving the distal shaft 24 with respect to the cervical canal CC. Alternatively, the treatment apparatus 10 can be used after performing an adjustment by moving the inflation portion 30 such that a protruding length of the distal shaft 24 is an appropriate length according to individual differences.

Next, the treatment method using the treatment apparatus 10 according to the embodiment will be described.

Figure 14:
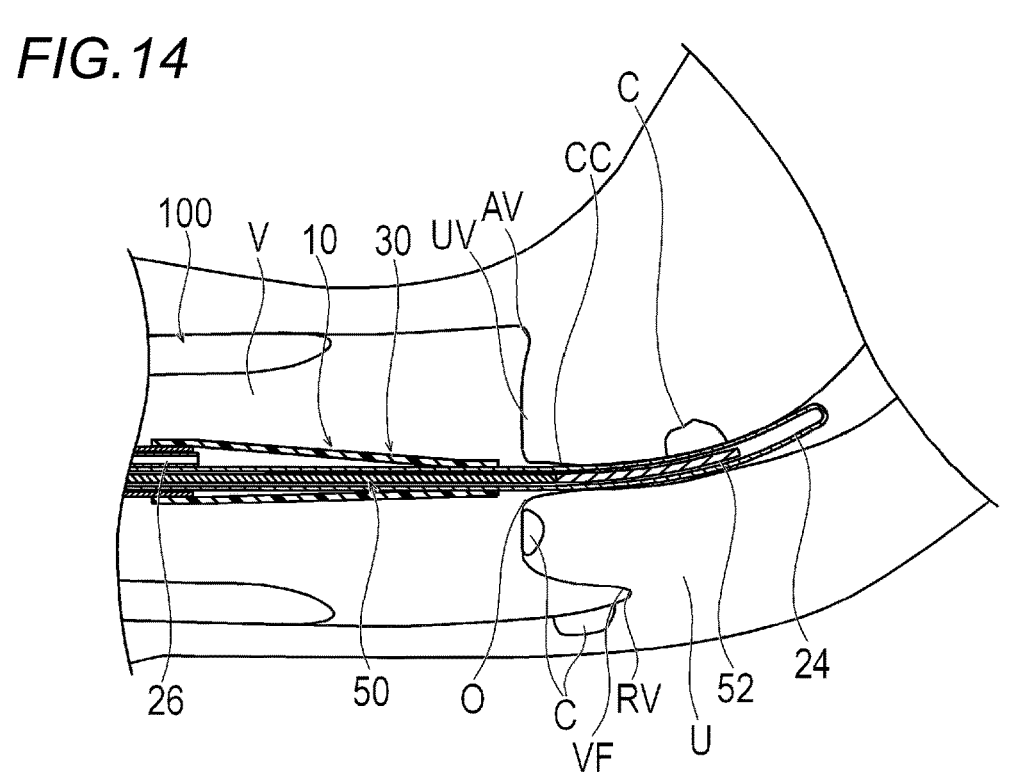
FIG. 14 is a schematic view illustrating a state in which the distal shaft of the treatment apparatus according to the embodiment is inserted into a cervical canal.

First, the antibody-photosensitive substance is administered intravenously. After approximately 12 hours to 36 hours from the intravenous administration, as illustrated in FIG. 14, the operator opens the vaginal introitus by using a vaginal speculum 100, and inserts the treatment apparatus 10 with the inflation portion 30 being deflated into the vagina V from the vaginal introitus. At this time, the operator inserts the treatment apparatus 10 starting from the distal shaft 24. Next, the operator inserts the distal portion of the distal shaft 24 from the external uterine ostium O into the cervical canal CC while visually checking the distal portion of the distal shaft 24. At this time, since the inflation portion 30 is not inflated, the operator can relatively easily insert the distal shaft 24 into the cervical canal CC.

Figure 15:
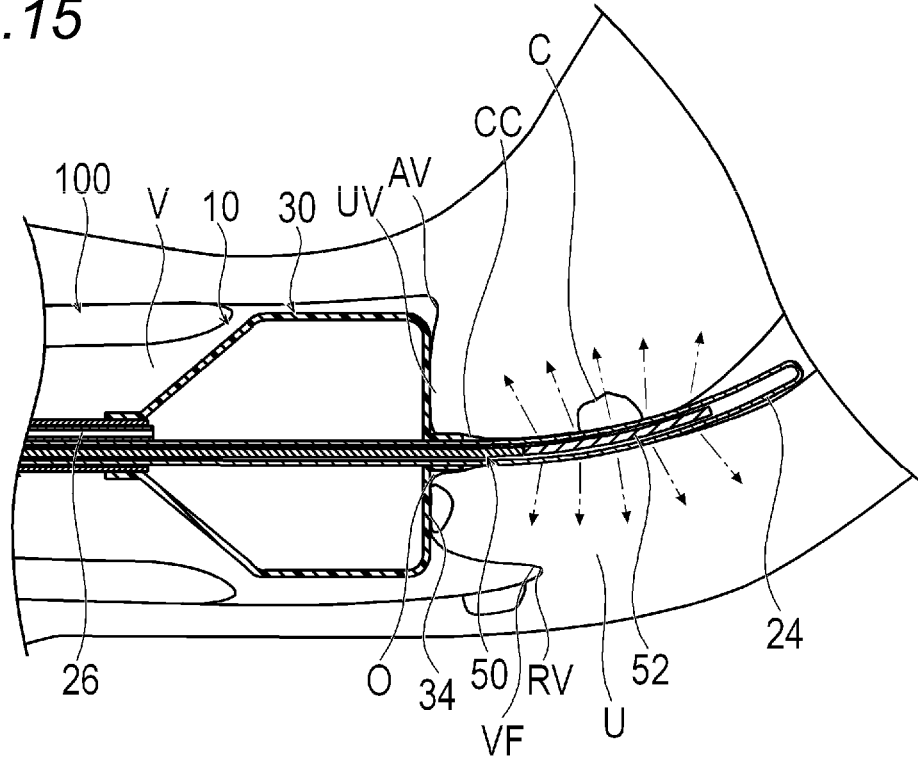
FIG. 15 is a schematic view illustrating a state in which near-infrared rays are emitted from the distal shaft inserted into the cervical canal to tumor cells.

Next, as illustrated in FIG. 15, the operator connects the syringe or the indeflator that accommodates a fluid such as air or a saline solution (saline) to the port 27, and supplies the inflation fluid into the inflation portion 30 via the inflation lumen 26. Accordingly, the inflation portion 30 is inflated in the vagina V. The inflation portion 30 is preferably inflated to such a degree that the inflation portion 30 is movable in the vagina V. Next, the operator pushes the operation portion 60, and presses the abutment surface 34 of the inflated inflation portion 30 against the uterine vagina UV. The uterine vagina UV is a portion of the cervix U that is closer to the vagina V, and includes the external uterine ostium O. When the inflation portion 30 comes into close contact with the uterine vagina UV, the distal shaft 24 is positioned within the cervical canal CC, and the inflation portion 30 is positioned within the vagina V. Next, the operator further inflates the inflation portion 30. Accordingly, the inflation portion 30 is inflated in a state of being in relatively close contact with the uterine vagina UV. The inflation portion 30 is inflated in accordance with the shape of the organ. As a result, a radially outer portion of the inflation portion 30 approaches the vaginal vault VF. Therefore, the radially outer portion of the inflation portion 30 can approach not only the anterior vaginal vault AV near the vaginal introitus but also the posterior vaginal vault RV far from the vaginal introitus. The inflation portion 30 may be inflated only once or may be inflated three or more times.

Next, the operator disposes the light-emitting unit 52 of the irradiation unit 50 inside the distal shaft 24. Thereafter, the operator operates the light output device 80 to supply near-infrared rays to the irradiation unit 50. Accordingly, the light-emitting unit 52 inside the distal shaft 24 can effectively emit the near-infrared rays to the tumor cells C positioned in the cervix U. An irradiation direction of the near-infrared rays from the light-emitting unit 52 includes a direction substantially perpendicular to an axial center of the distal shaft 24. Therefore, the light-emitting unit 52 can effectively emit the near-infrared rays from the cervical canal CC to the tumor cells C positioned in the cervix U. The operator may cause the near-infrared rays to be emitted while moving the light-emitting unit 52 inside the distal shaft 24.

When the near-infrared rays are emitted, the near-infrared rays reach the antibody-photosensitive substance bound to the tumor cells C in the cervix U. Accordingly, a chemical change occurs in the antibody-photosensitive substance that receives the near-infrared rays, which serve as the excitation light, and then the structural change occurs in the antibody-photosensitive substance, which generates holes in the cell membranes. Accordingly, the tumor cells C irradiated with the near-infrared rays can be destroyed.

When the operator determines that the tumor cells C are sufficiently destroyed or a predetermined time passes, the operator stops emitting the near-infrared rays.

Figure 16:
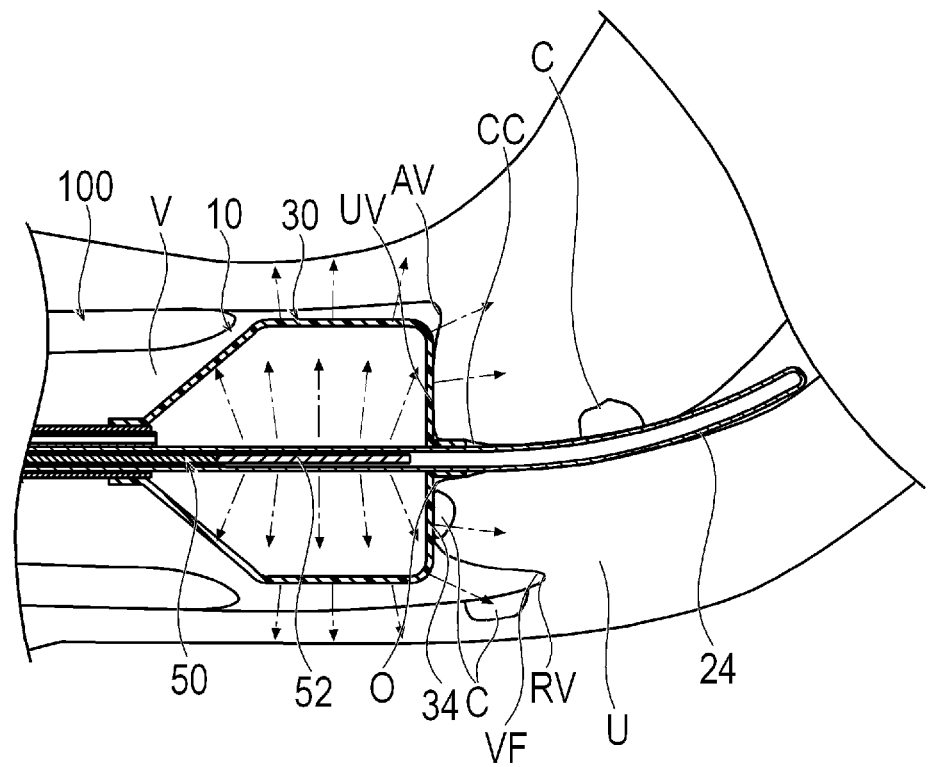
FIG. 16 is a schematic view illustrating a state in which the near-infrared rays are emitted from the inflation portion in the vagina to the tumor cells.

Next, as illustrated in FIG. 16, the operator pulls the irradiation unit 50 and moves the light-emitting unit 52 inside the inflation portion 30 in a state in which the distal shaft 24 and the inflation portion 30 are held. Thereafter, the operator operates the light output device 80 to supply the near-infrared rays to the irradiation unit 50. Accordingly, the entire inflation portion 30 that receives the light from the light-emitting unit 52 can emit light. That is, a part of the near-infrared rays that reaches the inflation portion 30 is transmitted through the inflation portion 30, and a part of the near-infrared rays that reaches the inflation portion 30 is scattered or reflected by the inflation portion 30, and then emitted to a wide range. When the inflation portion 30 includes a structure that improves an irradiation intensity in the distal direction (see FIGS. 7A, 7B, and 7C), the near-infrared rays are emitted in a direction substantially perpendicular to an axial center of the irradiation shaft 22 and the distal direction. Therefore, the light-emitting unit 52 and the inflation portion 30 can effectively emit the near-infrared rays to the tumor cells C positioned mainly at the external uterine ostium O, the uterine vagina UV, the vaginal vault VF, and a site or location that is near the vaginal vault VF and is on the vaginal introitus side relative to the vaginal vault VF of the vagina V. Multiple folds are present in a vaginal wall on the vaginal introitus side relative to the vaginal vault VF of the vagina V, and by inflating the inflation portion 30 near the uterine vagina UV, incident angles of the near-infrared rays to the vaginal wall become relatively small. Therefore, reflection of light can be reduced as much as possible, and the near-infrared rays can be effectively emitted to the tumor cells C. The operator may cause the near-infrared rays to be emitted while moving the light-emitting unit 52 inside the inflation portion 30. The operator may cause the near-infrared rays to be emitted while alternately moving the light-emitting unit 52 between the inside of the inflation portion 30 and the inside of the distal shaft 24. When the light-emitting unit 52 is elongated in the axial center direction and can emit light simultaneously from both the distal shaft 24 and the inflation portion 30, the operator does not need to move the light-emitting unit 52 between the distal shaft 24 and the inflation portion 30.

When the near-infrared rays are emitted, the near-infrared rays mainly reach the antibody-photosensitive substance bound to the tumor cells C in the external uterine ostium O, the uterine vagina UV, the vaginal vault VF, and the site or location that is near the vaginal vault VF and is on the vaginal introitus side relative to the vaginal vault VF of the vagina V. Accordingly, the chemical change occurs in the antibody-photosensitive substance that receives the near-infrared rays, which serve as the excitation light, and then the structural change occurs in the antibody-photosensitive substance, which generates holes in the cell membranes. Accordingly, the tumor cells C irradiated with the near-infrared rays are destroyed.

When the operator determines that the tumor cells C are sufficiently destroyed or a predetermined time passes, the operator stops emitting the near-infrared rays. Thereafter, the operator deflates the inflation portion 30, and draws the treatment apparatus 10 out of the cervical canal CC and the vagina V. Accordingly, this treatment method ends.

As described above, the treatment apparatus 10 according to the present embodiment is the treatment apparatus 10 for cervical cancer. The treatment apparatus 10 can include: the main shaft 21 including the distal portion and the proximal portion; the inflation portion 30 disposed on the distal side of the main shaft 21 and configured to be inflated by inflowing the fluid; the distal shaft 24 protruding from the inflation portion 30 toward the distal side; and at least one irradiation unit 50 configured to emit the excitation light of the antibody-photosensitive substance from the distal shaft 24 and the inflation portion 30.

According to the treatment apparatus 10 described above, the excitation light can be effectively emitted to the antibody-photosensitive substance bound to the tumor cells C in a wide range from the cervix U to the vagina V in a state in which the distal shaft 24 is inserted into the cervical canal CC and the inflation portion 30 is inflated in the vagina V. Therefore, this treatment method can improve a treatment effect of cancer in a wide range including the cervix U, the external uterine ostium O, the uterine vagina UV around the external uterine ostium O, the vaginal vault VF, and the site or location that is near the vaginal vault VF on the vaginal introitus side relative to the vaginal vault VF of the vagina V.

The distal shaft 24 emits the excitation light in a direction substantially perpendicular to the axial center of the distal shaft 24, and the inflation portion 30 emits the excitation light in a substantially distal direction. Accordingly, the excitation light can be emitted to the tumor cells C of the cervix U from both the distal shaft 24 and the inflation portion 30, and thus the treatment effect can be improved.

The treatment apparatus 10 is formed with the irradiation lumen 25 communicating with the inside of the inflation portion 30 and the inside of the distal shaft 24 and configured to movably accommodate the irradiation unit 50. Accordingly, the excitation light can be emitted from the distal shaft 24 and the inflation portion 30 with one irradiation unit 50, and thus a configuration of the treatment apparatus 10 can be simplified and operability can be improved. By moving the irradiation unit 50, a position where the excitation light is emitted can be appropriately adjusted, and thus the treatment effect can be improved.

The inflation portion 30 may have the abutment surface 34 facing the distal side in the inflated state of inflation portion 30, and the abutment surface 34 may have a portion that is separated from the axial center of the distal shaft 24 and that partially protrudes toward the distal side. Accordingly, by abutting the inflation portion 30 against the uterine vagina UV, the portion of the abutment surface 34 that protrudes toward the distal side can be brought relatively close to the vaginal vault VF. Therefore, the excitation light can be effectively emitted to the vicinity of the vaginal vault VF, which is difficult for light to reach, and the treatment effect can be improved.

The treatment apparatus 10 may further include the annular reinforcement portion 70 disposed on the distal side of the inflation portion 30 and surrounding the proximal portion of the distal shaft 24. Accordingly, the distal shaft 24 and the inflation portion 30 can be positioned at appropriate positions by inserting the distal shaft 24 into the cervical canal CC and abutting the reinforcement portion 70 against the uterine vagina UV. Therefore, the excitation light can be emitted from the distal shaft 24 and the inflation portion 30 to desired positions, and thus the treatment effect can be improved.

The inflation portion 30 may be configured to move relative to the main shaft 21 in the axial center direction of the main shaft 21. Accordingly, the distal shaft 24 can be inserted into the cervical canal CC in a state in which the inflation portion 30 is retracted toward the proximal side with respect to the main shaft 21 to secure the visual field. In a state in which the distal shaft 24 is maintained at an appropriate position of the cervical canal CC, the inflation portion 30 can be moved and disposed at an appropriate position. Therefore, both the distal shaft 24 and the inflation portion 30 can be relatively accurately and easily disposed at appropriate positions of the cervical canal CC and the vagina V. Therefore, the excitation light can be emitted from the distal shaft 24 and the inflation portion 30 to desired positions, and thus the treatment effect can be improved.

The treatment method according to the present embodiment is a treatment method for cervical cancer. The treatment method includes: intravenously administering the antibody-photosensitive substance; inserting the treatment apparatus 10 into the vagina V after 12 hours to 36 hours from the intravenous administration, the treatment apparatus 10 including the inflation portion 30 configured to be inflated and the distal shaft 24 protruding from the inflation portion 30 and configured to emit the excitation light of the antibody-photosensitive substance; inserting the distal shaft 24 into the cervical canal CC; inflating the inflation portion 30 in the vagina V; emitting the excitation light from the distal shaft 24 to a surrounding tissue; emitting the excitation light from the inflation portion 30 to a surrounding tissue; and deflating the inflation portion 30.

According to the treatment method described above, the distal shaft 24 can be inserted into the cervical canal CC from the external uterine ostium O while visually checking the distal shaft 24 in a state in which the inflation portion 30 is deflated to secure the visual field, and the inflation portion 30 can be widely inflated in the vagina V. Therefore, by emitting the excitation light of the antibody-photosensitive substance from the distal shaft 24 and the inflation portion 30, the excitation light can be effectively emitted to the antibody-photosensitive substance bound to the tumor cells C in a wide range from the cervix U to the vagina V. Therefore, this treatment method can improve the treatment effect of cancer in a relatively wide range from the cervix U to the vagina V.

In the emitting of the excitation light from the distal shaft 24, the irradiation unit 50 configured to emit the excitation light may be disposed inside the distal shaft 24 to emit the excitation light from the irradiation unit 50. In the emitting of the excitation light from the inflation portion 30, the irradiation unit 50 may be disposed inside the inflation portion 30 to emit the excitation light from the irradiation unit 50. The irradiation unit 50 may be moved between the distal shaft 24 and the inflation portion 30 between the emitting of the excitation light from the distal shaft 24 and the emitting of the excitation light from the inflation portion 30. Accordingly, even if only one irradiation unit 50 is provided, the excitation light can be emitted from the distal shaft 24 and the inflation portion 30, and thus the configuration of the treatment apparatus 10 can be relatively simplified and the operability can be improved. By moving the irradiation unit 50, a position where the excitation light is emitted can be appropriately adjusted, and thus the treatment effect can be improved. An order of emitting the excitation light is not limited. Therefore, the excitation light may be emitted from the distal shaft 24 first, or the excitation light may be emitted from the inflation portion 30 first.

The emitting of the excitation light from the distal shaft 24 and the emitting of the excitation light from the inflation portion 30 may be performed simultaneously. Accordingly, this treatment method can simultaneously emit the excitation light from various positions and directions, and thus the treatment effect can be improved, and treatment can be efficiently performed in a relatively short time.

In the inserting of the distal shaft 24 into the cervical canal CC, the abutment surface 34 may be abutted against the uterine vagina UV. The abutment surface 34 is disposed on the proximal side of the distal shaft 24. The distal shaft 24 extends from the abutment surface 34, and faces the distal side. Accordingly, the distal shaft 24 and the inflation portion 30 can be positioned at appropriate positions. Therefore, the excitation light can be emitted from the distal shaft 24 and the inflation portion 30 to desired positions, and the treatment effect can be improved.

The disclosure is not limited to the embodiments described above, and various modifications can be made by those skilled in the art within a scope of the technical idea of the disclosure.

Figure 17:
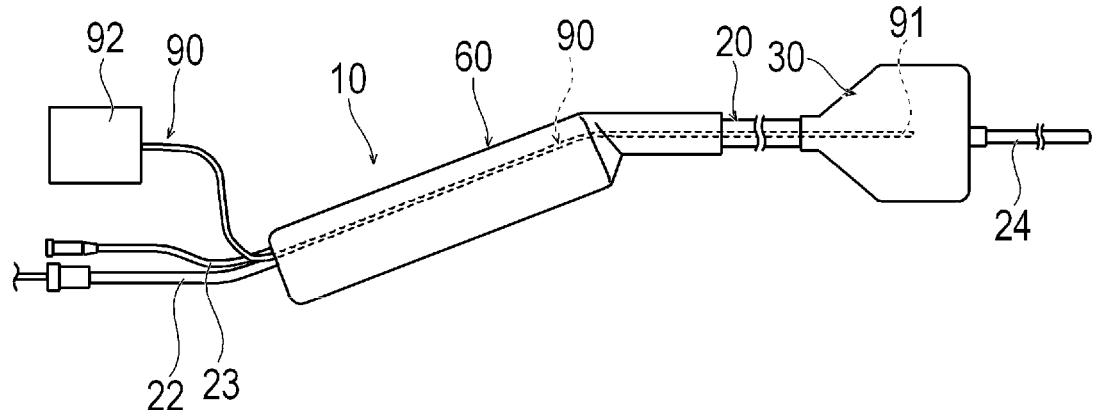
FIG. 17 is a plan view illustrating a treatment apparatus according to a 25th modification.

For example, as illustrated in FIG. 17, the treatment apparatus 10 may further include the detection unit 90 configured to detect fluorescence that is emitted by the antibody-photosensitive substance excited by being irradiated with near-infrared rays from the light-emitting unit 52 and has a wavelength (for example, 704 nm) different from a wavelength of irradiation light (for example, 689 nm). The detection unit 90 can include, for example, an optical waveguide 91 such as an optical fiber disposed in the irradiation lumen 25 like the irradiation unit 50 and receiving light, and an optical sensor 92 capable of detecting the amount of light. The detection unit 90 may include, at a position where the detection unit 90 receives light, a semiconductor sensor such as a complementary metal-oxide semiconductor (CMOS) image sensor that senses the light and converts the light into an electrical signal.

When the antibody-photosensitive substance bound to the tumor cells C is irradiated with the near-infrared rays, the antibody-photosensitive substance causes a photoreaction to emit the fluorescence, and destroys the tumor cells C. The antibody-photosensitive substance stops emitting the fluorescence after the tumor cells C are destroyed. Therefore, a degree of destruction of the tumor cells C due to the emission of the excitation light can be checked by measuring a change in an intensity of the detected fluorescence by the optical sensor 92. Therefore, a progress state of the photoreaction for destroying the tumor cells C can be checked.

The detection unit 90 may be a device different from the treatment apparatus 10 including the irradiation unit 50 described above as long as the detection unit 90 can detect the fluorescence emitted by the antibody-photosensitive substance excited by receiving the near-infrared rays. The detection unit 90 may be inserted into the vagina V, a uterus, a rectum, a bladder, a urethra, an abdominal cavity, a blood vessel, a ureter, or the like to detect fluorescence. The detection of the fluorescence by the detection unit 90 may be performed in parallel with the emission of the near-infrared rays by the treatment apparatus 10, or may be performed after the emission of the near-infrared rays by the treatment apparatus 10 is ended. The detection unit 90 may be inserted into the vagina V or the cervical canal CC after the treatment apparatus 10 is drawn out of the cervical canal CC and the vagina V. The detection unit 90 may detect fluorescence from a body surface outside a body in parallel with the emission of the near-infrared rays by the treatment apparatus 10 or after the emission of the near-infrared rays.

When the operator inserts the treatment apparatus 10 into the vagina V or the cervical canal CC, the detection unit 90 may be used to check a length of insertion of the treatment apparatus 10. For example, a position of the treatment apparatus 10 can be checked based on an image obtained from the CMOS image sensor or a change in the intensity or color of light obtained from the optical waveguide 91 such as an optical fiber.

Figure 18:
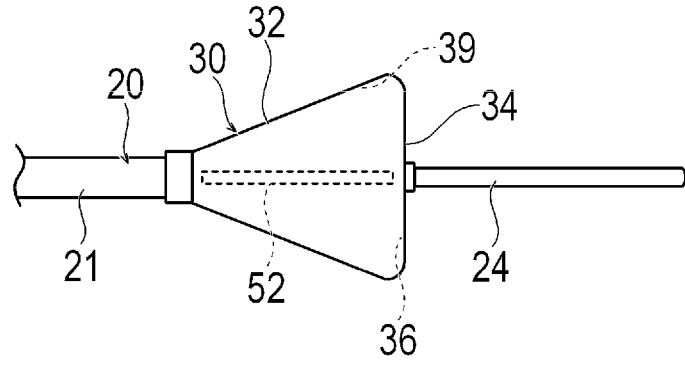
FIG. 18 is a plan view illustrating a treatment apparatus according to a 26th modification.

As illustrated in FIG. 18, the inflation portion 30 may not include a portion substantially parallel to and being in contact with the vaginal wall between the proximal inflation portion 32 and the abutment surface 34. An inner surface of the abutment surface 34 is coated with the scatterer coat 36, and the proximal inflation portion 32 whose outer diameter gradually decreases toward the proximal side is coated with the reflector coat 39. Accordingly, the light-emitting unit 52 emits light inside the inflation portion 30, and the excitation light emitted from the inflation portion 30 is reflected and diffused only in the distal direction (a direction in which the external uterine ostium O and the uterine vagina UV are present with respect to the inflation portion 30) and then emitted. Accordingly, the distal direction can be efficiently irradiated with light energy, and the treatment effect in the external uterine ostium O and the uterine vagina UV can be improved. The entire light-emitting unit 52 is preferably positioned within a range of a length of the inflation portion 30 in the axial center direction (a long axis direction). Accordingly, the light emitted from the light-emitting unit 52 can be input into the inflation portion 30 without waste.

The detailed description above describes embodiments of a treatment apparatus and a treatment method for cervical cancer and vaginal cancer. These disclosed embodiments represent examples of the treatment apparatus and the treatment method for cervical cancer and vaginal cancer disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment apparatus configured to irradiate an antibody-photosensitive substance bound to a tumor cell with excitation light, the treatment apparatus comprising:
a main shaft including a distal end portion and a proximal end portion;
an inflation portion disposed distal of the main shaft and configured to be inflated by inflowing a fluid, a proximal end portion of the inflation portion is fixed to the distal end portion of the main shaft;
an irradiation shaft accommodated in the main shaft, the irradiation shaft protruding from the distal end portion of the main shaft, passing through an inside of the inflation portion and extending beyond a distal end of the inflation portion so as to form a distal shaft that is a portion of the irradiation shaft protruding from the distal end of the inflation portion;
at least one irradiation unit including a light-emitting unit at a distal portion of the irradiation unit, the light-emitting unit configured to emit outward the excitation light of the antibody-photosensitive substance;
wherein the irradiation shaft includes an irradiation lumen that is closed at a most distal end of the irradiation shafter and opened at a most proximal end of the irradiation shaft, the irradiation lumen passing through the inside of the inflation portion to an inside of the distal shaft and configured to movably accommodate the irradiation unit;
an insertion port for receiving the irradiation unit into the irradiation lumen is disposed on a proximal side of the irradiation shaft;
the distal shaft includes the most distal end of the irradiation shaft, which closes a distal end of the irradiation lumen and protrudes distally relative to the distal end of the inflation portion by a predetermined protrusion length in a range of 10 mm to 50 mm;
wherein an outer diameter of the distal shaft is smaller than a maximum outer diameter of the inflation portion when being inflated the inflation portion; and wherein the light-emitting unit of the irradiation unit is configured to be disposed in a first portion of the irradiation lumen disposed on the inside of the inflation portion and a second portion of the irradiation lumen disposed on the inside of the distal shaft, so as to emit the excitation light of the antibody-photosensitive substance from the inflation portion and the distal shaft.

2. The treatment apparatus according to claim 1, wherein the distal shaft is configured to emit the excitation light in a direction substantially perpendicular to an axial center of the distal shaft; and
the inflation portion is configured to emit the excitation light in a substantially distal direction.

3. The treatment apparatus according to claim 1, wherein the inflation portion has an abutment surface facing the distal side of the inflation portion in an inflated state of the inflation portion; and
the abutment surface has a portion that is separated from an axial center of the distal shaft and that partially protrudes toward the distal side.

4. The treatment apparatus according to claim 1, further comprising:
an annular reinforcement portion disposed on a distal side of the inflation portion and surrounding a proximal portion of the distal shaft.

5. The treatment apparatus according to claim 1, wherein the inflation portion is configured to move relative to the main shaft in an axial center direction of the main shaft.

6. The treatment apparatus according to claim 1, wherein the light-emitting unit of the irradiation unit is configured to move from the first portion of the irradiation lumen to the second portion of the irradiation lumen.

7. The treatment apparatus according to claim 1, wherein the distal shaft includes a bent portion such that an axial center of a distal portion of the distal shaft is bent at an angle of less than 90° with respect to an axial center of a proximal portion of the distal shaft.

8. A treatment method, comprising:
intravenously administering an antibody-photosensitive substance;
inserting a treatment apparatus into a living body after 12 hours to 36 hours from the intravenous administration of the antibody-photosensitive substance, the treatment apparatus including a main shaft including a distal end portion and a proximal end portion, an inflation portion disposed distal of the main shaft and configured to be inflated by inflowing a fluid, a proximal end portion of the inflation portion is fixed to the distal end portion of the main shaft, an irradiation shaft accommodated in the main shaft, the irradiation shaft protruding from the distal end portion of the main shaft, passing through an inside of the inflation portion and extending beyond a distal end of the inflation portion so as to form a distal shaft that is a portion of the irradiation shaft protruding from the distal end of the inflation portion, and at least one irradiation unit including a light-emitting unit at a distal portion of the irradiation unit, the light-emitting unit configured to emit outward the excitation light of the antibody-photosensitive substance, and wherein the irradiation shaft includes an irradiation lumen that is closed at a most distal end of the irradiation shaft and opened at a most proximal end of the irradiation shaft, the irradiation lumen passing through the inside of the inflation portion to an inside of the distal shaft and configured to movably accommodate the irradiation unit, an insertion port for receiving the irradiation unit into the irradiation lumen is disposed on a proximal side of the irradiation shaft, the distal shaft includes the most distal end of the irradiation shaft, which closes a distal end of the irradiation lumen and protrudes distally relative to the distal end of the inflation portion by a predetermined protrusion length in a range of 10 mm to 50 mm, wherein an outer diameter of the distal shaft is smaller than a maximum outer diameter of the inflation portion when being inflated the inflation portion, wherein the light-emitting unit of the irradiation unit is configured to be disposed in a first portion of the irradiation lumen disposed on the inside of the inflation portion and a second portion of the irradiation lumen disposed on the inside of the distal shaft, so as to emit the excitation light of the antibody-photosensitive substance from the inflation portion and the distal shaft;

inserting the distal shaft into a body lumen;

inflating the inflation portion in the living body;

emitting the excitation light from the distal shaft to a surrounding tissue;

emitting the excitation light from the inflation portion to the surrounding tissue; and deflating the inflation portion.

9. The treatment method according to claim 8, further comprising:

simultaneously performing the emitting of the excitation light from the distal shaft and the emitting of the excitation light from the inflation portion.

10. The treatment method according to claim 8, wherein the body lumen is a cervical canal, and wherein in the inserting of the distal shaft into the cervical canal, the method further comprises:

abutting an abutment surface against a uterine vagina, the abutment surface being disposed on a proximal side of the distal shaft, the distal shaft extending from the abutment surface and the abutment surface facing a distal side of the distal shaft.

11. The treatment method according to claim 8, further comprising:

detecting fluorescence emitted by the antibody-photosensitive substance and checking an intensity of the fluorescence.

12. The treatment method according to claim 8, wherein the living body is a vagina of a patient, and the body lumen is a cervical canal of the patient.

13. The treatment method according to claim 8, further comprising:

treating the surrounding tissue for cervical cancer.

14. The treatment method according to claim 8, further comprising:

moving the light-emitting unit of the irradiation unit from the first portion of the irradiation lumen to the second portion of the irradiation lumen.

15. The treatment method according to claim 8, wherein the distal shaft includes a bent portion such that an axial center of a distal portion of the distal shaft is bent at an angle of less than 90° with respect to an axial center of a proximal portion of the distal shaft.

16. A treatment method comprising:

intravenously administering an antibody-photosensitive substance;

inserting a treatment apparatus into a living body after the intravenous administration of the antibody-photosensitive substance, the treatment apparatus including a main shaft including a distal end portion and a proximal end portion, an inflation portion disposed distal of the main shaft and configured to be inflated by inflowing a fluid, a proximal end portion of the inflation portion is fixed to the distal end portion of the main shaft, an irradiation shaft accommodated in the main shaft, the irradiation shaft protruding from the distal end portion of the main shaft, passing through an inside of the inflation portion and extending beyond a distal end of the inflation portion so as to form a distal shaft that is a portion of the irradiation shaft protruding from the distal end of the inflation portion, and at least one irradiation unit including a light-emitting unit at a distal portion of the irradiation unit, the light-emitting unit configured to emit outward the excitation light of the antibody-photosensitive substance, and wherein the irradiation shaft includes an irradiation lumen that is closed at a most distal end of the irradiation shaft and opened at a most proximal end of the irradiation shaft, the irradiation lumen passing through the inside of the inflation portion to an inside of the distal shaft and configured to movably accommodate the irradiation unit, an insertion port for receiving the irradiation unit into the irradiation lumen is disposed on a proximal side of the irradiation shaft, the distal shaft includes the most distal end of the irradiation shaft, which closes a distal end of the irradiation lumen and protrudes distally relative to the distal end of the inflation portion by a predetermined protrusion length in a range of 10 mm to 50 mm, wherein an outer diameter of the distal shaft is smaller than a maximum outer diameter of the inflation portion when being inflated the inflation portion, wherein the light-emitting unit of the irradiation unit is configured to be disposed in a first portion of the irradiation lumen disposed on the inside of the inflation portion and a second portion of the irradiation lumen disposed on the inside of the distal shaft, so as to emit the excitation light of the antibody-photosensitive substance from the inflation portion and the distal shaft;

inserting the distal shaft into a body lumen;

inflating the inflation portion in the living body; and emitting the excitation light from the distal shaft and the inflation portion to surrounding tissue.

17. The treatment method according to claim 16, further comprising:

simultaneously performing the emitting of the excitation light from the distal shaft and the emitting of the excitation light from the inflation portion.

18. The treatment method according to claim 16, further comprising:

detecting fluorescence emitted by the antibody-photosensitive substance and checking an intensity of the fluorescence.

19. The treatment method according to claim 16, further comprising:

moving the light-emitting unit of the irradiation unit from the first portion of the irradiation lumen to the second portion of the irradiation lumen.

20. The treatment method according to claim 16, wherein the distal shaft includes a bent portion such that an axial center of a distal portion of the distal shaft is bent at an angle of less than 90° with respect to an axial center of a proximal portion of the distal shaft.

* * * * *